United States Patent
Endo et al.

(10) Patent No.: US 12,366,804 B2
(45) Date of Patent: Jul. 22, 2025

(54) COMPOSITION CONTAINING A HETEROCYCLIC COMPOUND HAVING A DICYANOSTYRYL GROUP, FOR FORMING A RESIST UNDERLAYER FILM CAPABLE OF BEING WET ETCHED

(71) Applicant: NISSAN CHEMICAL CORPORATION, Tokyo (JP)

(72) Inventors: Takafumi Endo, Toyama (JP); Yuki Endo, Toyama (JP)

(73) Assignee: NISSAN CHEMICAL CORPORATION, Tokyo (JP)

( * ) Notice: Subject to any disclaimer, the term of this patent is extended or adjusted under 35 U.S.C. 154(b) by 781 days.

(21) Appl. No.: 17/619,542

(22) PCT Filed: Jun. 17, 2020

(86) PCT No.: PCT/JP2020/023670
§ 371 (c)(1),
(2) Date: Dec. 15, 2021

(87) PCT Pub. No.: WO2020/255984
PCT Pub. Date: Dec. 24, 2020

(65) Prior Publication Data
US 2022/0319839 A1    Oct. 6, 2022

(30) Foreign Application Priority Data
Jun. 17, 2019  (JP) .................. 2019-111915

(51) Int. Cl.
G03F 7/09 (2006.01)
C07D 251/34 (2006.01)
G03F 7/11 (2006.01)
G03F 7/36 (2006.01)
H01L 21/027 (2006.01)

(52) U.S. Cl.
CPC .......... *G03F 7/091* (2013.01); *C07D 251/34* (2013.01); *G03F 7/11* (2013.01); *G03F 7/36* (2013.01); *H01L 21/0274* (2013.01)

(58) Field of Classification Search
CPC .......... G03F 7/091; G03F 7/11; C07D 251/34
See application file for complete search history.

(56) References Cited

U.S. PATENT DOCUMENTS

| 5,218,136 A * | 6/1993 | Yamamoto ............ C07C 255/42 558/402 |
| 2004/0058275 A1 | 3/2004 | Neef et al. |
| 2019/0129305 A1 | 5/2019 | Lee et al. |
| 2020/0354501 A1 | 11/2020 | Makinoshima et al. |

FOREIGN PATENT DOCUMENTS

| JP | H11-511194 A |   | 9/1999 |
| JP | 2006-508377 A |   | 3/2006 |
| JP | 2009204985 A | * | 9/2009 |
| JP | 2019-082682 A |   | 5/2019 |
| WO | 97/007145 A1 |   | 2/1997 |
| WO | 2019/098338 A1 |   | 5/2019 |

OTHER PUBLICATIONS

Sep. 1, 2020 International Search Report issued in International Patent Application No. PCT/JP2020/023670.
Dec. 21, 2021 International Preliminary Report on Patentability issued in International Patent Application No. PCT/JP2020/023670.

* cited by examiner

*Primary Examiner* — John S. Chu
(74) *Attorney, Agent, or Firm* — Oliff PLC

(57) ABSTRACT

A resist underlayer film, which while exhibiting excellent resistance to a resist developer which is a resist solvent or an alkaline aqueous solution, exhibits removability, and preferably solubility, only in wet etching chemicals. This composition for forming a resist underlayer film contains a solvent, a heterocyclic compound having a dicyanostyryl group, a cyclic compound including an amide group, for example, and the reaction product of a heterocyclic compound precursor having an epoxy group and an active proton compound, for example.

16 Claims, No Drawings

COMPOSITION CONTAINING A HETEROCYCLIC COMPOUND HAVING A DICYANOSTYRYL GROUP, FOR FORMING A RESIST UNDERLAYER FILM CAPABLE OF BEING WET ETCHED

TECHNICAL FIELD

The present invention relates to a resist underlayer film-forming composition, a resist underlayer film obtained from the resist underlayer film-forming composition, a method for producing a patterned substrate and a method for producing a semiconductor device, each using the resist underlayer film-forming composition, and a heterocyclic compound having a dicyanostyryl group, and a method for producing the same.

BACKGROUND ART

A lithography process in the production of a semiconductor has been widely known, in which a resist underlayer film is formed between a substrate and a resist film formed on the substrate, forming a resist pattern having a desired form. After forming the resist pattern, removal of the resist underlayer film and processing of the substrate are conducted, and, in these steps, dry etching is mainly used. Further, after processing the substrate, in the step of removing the unnecessary resist pattern and the resist underlayer film, dry etching is used, but, for the purpose of simplifying the steps for process and reducing a damage to the processed substrate, wet etching using a chemical liquid is often used.

Patent Literature 1 discloses an improved ARC composition comprising:
 a. a dye-grafted hydroxyl-functional oligomer reaction product of a preliminarily selected phenol- or carboxylic acid-functional dye and a poly(epoxide) resin having an epoxy functionality of more than 2.0 to less than 10, wherein the reaction product has light-absorption properties effective for ARC application of a ground layer;
 b. an alkylated aminoplast crosslinking agent derived from melamine, urea, benzoguanamine, or glycoluril;
 c. a protonic acid curing catalyst; and
 d. a solvent system comprising a low- or medium-boiling point alcohol, wherein the alcohol occupies at least 20% by weight of the total solvent amount in the solvent system, and the molar ratio of the alcohol and the equivalent methylol unit of the aminoplast is at least 4:1,
 the improved ARC composition having:
 e. an ether or ester linkage derived from a poly(epoxide) molecule,
 wherein the improved ARC prevents mixing of the resist/ARC components by virtue of the thermosetting action of ARCs and provides an improved optical concentration in the target exposure and ARC layer thickness, and nullifies a need of a high molecular-weight thermoplastic ARC binder exhibiting a high solubility difference.

However, there is neither disclosure of a poly(epoxide) resin having an epoxy functionality of 10 or more nor disclosure of an epoxy compound containing a heterocyclic compound.

CITATION LIST

Patent Literature

Patent Literature 1: JP H11-511194 A

SUMMARY OF INVENTION

Technical Problem

A resist is applied onto a resist underlayer film, and subjected to exposure using a radiation (for example, an ArF excimer laser, a KrF excimer laser, or an i-line) and development to obtain a desired resist pattern, and the resist underlayer film used in this case is required to have such excellent resist solvent resistance that the film suffers no peeling or damage due to a resist solvent. The resist underlayer film is further required to have such excellent resist developer resistance that the film suffers no peeling or damage due to a resist developer (aqueous alkali solution) mainly used in the resist development step. Further, for obtaining a desired resist pattern, the resist underlayer film is needed to have such antireflection performance that the film can suppress reflection from the substrate with respect to the radiation used in the lithography process to prevent the resist pattern from deteriorating due to a standing wave. Moreover, when the resist underlayer film is removed by dry etching, the resist underlayer film is needed to have such a fast etching rate (high etching rate) that the resist underlayer film can be quickly removed by dry etching so as not to damage the substrate. Particularly, when the resist underlayer film is removed by wet etching using a chemical liquid, the resist underlayer film is required to exhibit satisfactory solubility in the wet etching chemical liquid such that the resist underlayer film can be easily removed from the substrate.

On the other hand, in the wet etching chemical liquid for removing the resist and resist underlayer film, for reducing a damage to the processed substrate, an organic solvent is used. Further, for improving the removal properties for the resist and resist underlayer film, a basic organic solvent is used. However, it is difficult for the conventional technique to achieve a resist underlayer film which has excellent resistance to a resist solvent that is mainly an organic solvent and to a resist developer that is an aqueous alkali solution, and which further exhibits removability only by a wet etching chemical liquid, preferably solubility only in a wet etching chemical liquid. An object of the present invention is to solve the above-mentioned problems.

Solution to Problem

The present invention encompasses the followings.
 [1] A resist underlayer film-forming composition comprising a solvent and a heterocyclic compound having a dicyanostyryl group.
 [2] The resist underlayer film-forming composition according to [1], wherein the heterocyclic compound having a dicyanostyryl group is a cyclic compound containing an amide group.
 [3] The resist underlayer film-forming composition according to [1] or [2], wherein the heterocyclic compound having a dicyanostyryl group is a reaction product of an active proton compound and a heterocyclic compound precursor having an epoxy group.

[4] The resist underlayer film-forming composition according to [1] or [2], wherein the dicyanostyryl group is represented by the following formula (1):

[Chemical formula 1]

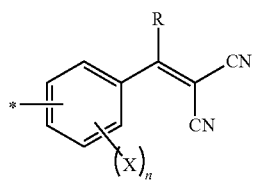

Formula (1)

wherein X represents an alkyl group, a hydroxy group, an alkoxy group, an alkoxycarbonyl group, a halogen atom, a cyano group, or a nitro group; R represents a hydrogen atom, an alkyl group, or an arylene group; n represents an integer of 0 to 4; and * indicates a bonding site to the heterocyclic compound.

[5] The resist underlayer film-forming composition according to [1], wherein the heterocyclic compound having a dicyanostyryl group is represented by the following formula (2):

[Chemical formula 2]

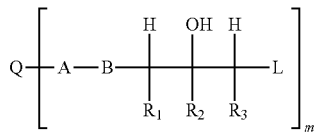

Formula (2)

wherein Q is a group resulting from eliminating m quantity of terminal atom or atoms from the heterocyclic compound, m an integer of 1 to 4, each of m quantity of A is independently a direct bond or an optionally branched and/or substituted alkylene group having 1 to 10 carbon atoms optionally interrupted with an ether linkage, a thioether linkage, or an ester linkage, each of m quantity of B independently represents a direct bond, an ether linkage, a thioether linkage, or an ester linkage, each of m quantity of $R_1$, $R_2$ and $R_3$ independently represents a hydrogen atom, a methyl group, or an ethyl group, and each of m quantity of L is independently represented by the following formula (3):

[Chemical formula 3]

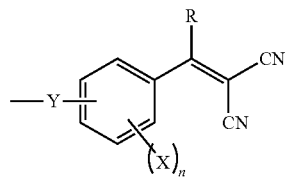

Formula (3)

wherein Y represents an ether linkage, a thioether linkage, or an ester linkage, R represents a hydrogen atom, an alkyl group, or an arylene group, n represents an integer of 0 to 4, and each of n quantity of X independently represents an alkyl group, a hydroxy group, an alkoxy group, an alkoxycarbonyl group, a halogen atom, a cyano group, or a nitro group.

[6] The resist underlayer film-forming composition according to any one of [1] to [4], wherein the heterocycle is triazinetrione.

[7] The resist underlayer film-forming composition according to [5], wherein the Q in formula (2) is triazinetrione.

[8] The resist underlayer film-forming composition according to [4] or [5], wherein the R in formula (1) and/or formula (3) is a hydrogen atom.

[9] The resist underlayer film-forming composition according to [5], wherein the Y in formula (3) represents an ether linkage or an ester linkage.

[10] The resist underlayer film-forming composition according to [5], wherein the A in formula (2) represents a direct bond.

[11] The resist underlayer film-forming composition according to any one of [1] to [10], further comprising a crosslinking agent and/or a crosslinking catalyst.

[12] The resist underlayer film-forming composition according to any one of [1] to [11], for use on a substrate having copper on the surface.

[13] A resist underlayer film provided by removing a solvent from an applied film comprising the resist underlayer film-forming composition according to any one of [1] to [12].

[14] The resist underlayer film according to [13] formed on a substrate having copper on the surface.

[15] A method for producing a patterned substrate, comprising the steps of:
applying the resist underlayer film-forming composition according to any one of [1] to [12] onto a substrate having copper on the surface and baking the applied composition to form a resist underlayer film;
applying a resist onto the resist underlayer film and baking the applied resist to form a resist film;
subjecting the semiconductor substrate covered with the resist underlayer film and the resist to exposure; and
subjecting the resist film obtained after exposure to development and patterning.

[16] A method for producing a semiconductor device, comprising the steps of:
forming a resist underlayer film comprising the resist underlayer film-forming composition according to any one of [1] to [12] on a substrate having copper on the surface;
forming a resist film on the resist underlayer film;
irradiating the resist film with a light or an electron beam and subjecting the resultant resist film to development to form a resist pattern;
then removing the resist underlayer film exposed between the resist pattern;
performing copper plating in the formed resist pattern, preferably in the resist pattern from which the resist underlayer film has been removed; and
removing the resist pattern and the resist underlayer film present under the resist pattern.

[17] The method according to [16], wherein at least one of the steps of removing the resist underlayer film is conducted by a wet treatment.

[18] A compound represented by the following formula (4):

[Chemical formula 4]

Formula (4)

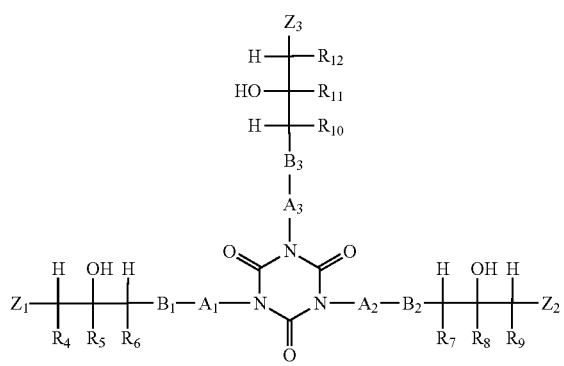

wherein each of $A_1$ to $A_3$ is independently a direct bond or an optionally substituted alkylene group having 1 to 6 carbon atoms,
each of $B_1$ to $B_3$ independently represents a direct bond, an ether linkage, a thioether linkage, or an ester linkage,
each of $R_4$ to $R_{12}$ independently represents a hydrogen atom, a methyl group, or an ethyl group, and
$Z_1$ to $Z_3$ are represented by the following formula (5):

[Chemical formula 5]

Formula (5)

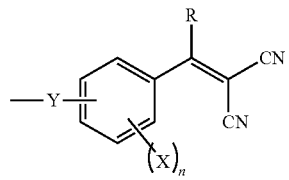

wherein each of n quantity of X independently represents an alkyl group, a hydroxy group, an alkoxy group, an alkoxycarbonyl group, a halogen atom, a cyano group, or a nitro group,
Y represents an ether linkage, a thioether linkage, or an ester linkage,
R represents a hydrogen atom, an alkyl group, or an arylene group, and
n represents an integer of 0 to 4.

[19] A method for producing a heterocyclic compound having a dicyanostyryl group, comprising the step of reacting a heterocyclic compound precursor having an epoxy group and a proton compound having a dicyanostyryl group.

[20] A method for producing a heterocyclic compound having a dicyanostyryl group, comprising the steps of:
reacting a heterocyclic compound precursor having an epoxy group with an active proton compound having a carbonyl group to obtain an intermediate; and
subjecting the intermediate to cyanation.

Advantageous Effects of Invention

In the present invention, there can be provided a resist underlayer film which has excellent resistance to a resist solvent that is mainly an organic solvent as well as to a resist developer that is an aqueous alkali solution, and which further exhibits removability only by a wet etching chemical liquid, preferably solubility only in a wet etching chemical liquid.

DESCRIPTION OF EMBODIMENTS

[Resist Underlayer Film-Forming Composition]
The resist underlayer film-forming composition of the present invention comprises a solvent and a heterocyclic compound having a dicyanostyryl group.
[Heterocyclic Compound Having a Dicyanostyryl Group]
The dicyanostyryl group in the present invention is a group represented by the following formula:

[Chemical formula 6]

Formula (1)

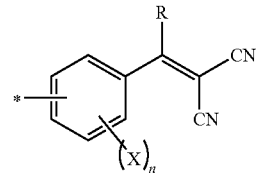

wherein X represents an alkyl group, a hydroxy group, an alkoxy group, an alkoxycarbonyl group, a halogen atom, a cyano group, or a nitro group; R represents a hydrogen atom, an alkyl group, or an arylene group; n represents an integer of 0 to 4; and * indicates a bonding site to the heterocyclic compound.

The heterocyclic compound in the present invention means a compound implied by the heterocyclic compound which is a term generally used in organic chemistry, and is not particularly limited. Examples of the heterocyclic compounds include furan, thiophene, pyrrole, imidazole, pyran, pyridine, pyrimidine, pyrazine, pyrrolidine, piperidine, piperazine, morpholine, quinuclidine, indole, purine, quinoline, isoquinoline, chromene, thianthrene, phenothiazine, phenoxazine, xanthene, acridine, phenazine, carbazole, hydantoin, triazine, and cyanuric acid.

The heterocyclic compound having a dicyanostyryl group is preferably a cyclic compound containing an amide group. Further, the heterocyclic compound having a dicyanostyryl group is preferably a reaction product of a heterocyclic compound precursor having an epoxy group with an active proton compound having a dicyanostyryl group, or a reaction product obtained by subjecting a reaction intermediate of a heterocyclic compound precursor having an epoxy group with an active proton compound having a carbonyl group to cyanation.

The active proton compound in the present invention means a compound implied by the active proton compound which is a term generally used in organic chemistry, and is not particularly limited.

Examples of the active proton compounds include a compound having a hydroxy group, a compound having a carboxy group, a compound having a thiol group, a compound having an amino group, and a compound having an imide group, but preferred is a compound having a hydroxy group or a carboxy group.

Examples of the carbonyl group in the active proton compound having a carbonyl group include a formyl group (aldehyde group) and a ketone group, but preferred is a formyl group.

The dicyanostyryl group is preferably represented by the following formula (1-1):

[Chemical formula 7]

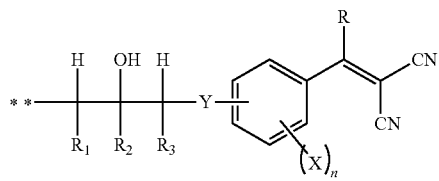

Formula (1-1)

wherein $R_1$ to $R_3$ represent a hydrogen atom, a methyl group, or an ethyl group, X represents an alkyl group, a hydroxy group, an alkoxy group, an alkoxycarbonyl group, a cyano group, or a nitro group, Y represents an ether linkage, a thioether linkage, or an ester linkage, R represents a hydrogen atom, an alkyl group, or an arylene group, n represents an integer of 0 to 4, and ** indicates a bonding site to the heterocyclic compound precursor.

The heterocycle is preferably triazinetrione. R in formula (1-1) is preferably a hydrogen atom. Y in formula (1-1) preferably represents an ether linkage or an ester linkage.

The heterocyclic compound having a dicyanostyryl group is preferably represented by the following formula (2):

[Chemical formula 8]

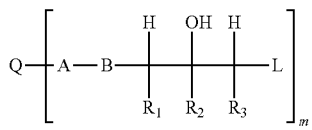

Formula (2)

wherein Q is a group resulting from eliminating m quantity of terminal atom or atoms from the heterocyclic compound, m represents an integer of 1 to 4, each of m quantity of A is independently a direct bond or an optionally branched and/or substituted alkylene group having 1 to 10 carbon atoms optionally interrupted with an ether linkage, a thioether linkage, or an ester linkage, each of m quantity of B independently represents a direct bond, an ether linkage, a thioether linkage, or an ester linkage, each of m quantity of $R_1$, $R_2$ and $R_3$ independently represents a hydrogen atom, a methyl group or an ethyl group, and each of m quantity of L is independently represented by the following formula (3):

[Chemical formula 9]

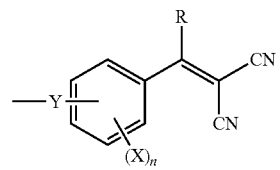

Formula (3)

wherein Y represents an ether linkage, a thioether linkage, or an ester linkage, R represents a hydrogen atom, an alkyl group, or an arylene group, n represents an integer of 0 to 4, and each of n quantity of X independently represents an alkyl group, a hydroxy group, an alkoxy group, an alkoxycarbonyl group, a halogen atom, a cyano group, or a nitro group.

Q in formula (3) is preferably triazinetrione. R in formula (3) is preferably a hydrogen atom. Y in formula (3) preferably represents an ether linkage or an ester linkage.

The heterocyclic compound having a dicyanostyryl group is preferably represented by the following formula (4):

[Chemical formula 10]

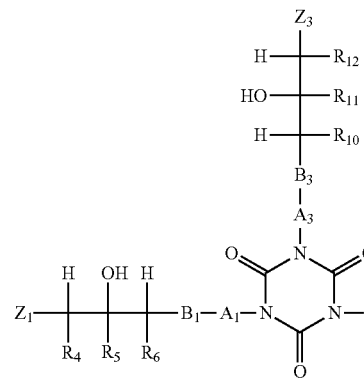

Formula (4)

wherein each of $A_4$ to $A_{12}$ is independently a direct bond or an optionally substituted alkylene group having 1 to 6 carbon atoms, each of $B_1$ to $B_3$ independently represents a direct bond, an ether linkage, a thioether linkage, or an ester linkage, each of $R_1$ to $R_9$ independently represents a hydrogen atom, a methyl group, or an ethyl group, and $X_1$ to $X_3$ are represented by the following formula (5):

[Chemical formula 11]

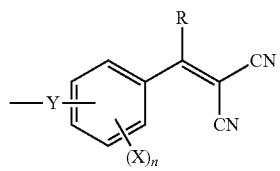

Formula (5)

wherein each of n quantity of X independently represents an alkyl group, a hydroxy group, an alkoxy group, an alkoxycarbonyl group, a halogen atom, a cyano group, or a nitro group, Y represents an ether linkage, a thioether linkage, or an ester linkage, R represents a hydrogen atom, an alkyl group, or an arylene group, and n represents an integer of 0 to 4.

Examples of the alkyl groups include optionally substituted, linear or branched alkyl groups, and examples include a methyl group, an ethyl group, a n-propyl group, an isopropyl group, a n-butyl group, a sec-butyl group, a tert-butyl group, a n-pentyl group, an isopentyl group, a neopentyl group, a n-hexyl group, an isohexyl group, a n-heptyl group, a n-octyl group, a cyclohexyl group, a 2-ethylhexyl group, a n-nonyl group, an isononyl group, a p-tert-butylcyclohexyl group, a n-decyl group, a n-dodecyl-nonyl group, an undecyl group, a dodecyl group, a tridecyl group, a tetradecyl group, a pentadecyl group, a hexadecyl group, a heptadecyl group, an octadecyl group, a nonadecyl group, and an eicosyl group. Preferred are alkyl groups having 1 to 20 carbon atoms, more preferred are alkyl groups having 1 to 12 carbon atoms, further preferred are alkyl groups having 1 to 8 carbon atoms, and most preferred are alkyl groups having 1 to 4 carbon atoms.

Examples of the alkoxy group include any group in which an oxygen atom is bonded to the above-mentioned alkyl group. Examples thereof include a methoxy group, an ethoxy group, a propoxy group, and a butoxy group.

Examples of the alkoxycarbonyl group include any groups, in which an oxygen atom and a carbonyl group are bonded to the above-mentioned alkyl groups. Examples thereof include a methoxycarbonyl group, an ethoxycarbonyl group, a propoxycarbonyl group, and a butoxycarbonyl group.

Examples of the alkylene group include any divalent groups, in which one more hydrogen atom is removed from the above-mentioned alkyl groups. Examples thereof include a methylene group, an ethylene group, a 1,3-propylene group, and a 1,2-propylene group.

Examples of the arylene groups include a phenylene group, an o-methylphenylene group, a m-methylphenylene group, a p-methylphenylene group, an α-naphthylene group, a β-naphthylene group, an o-biphenylylene group, a m-biphenylylene group, a p-biphenylylene group, a 1-anthrylene group, a 2-anthrylene group, a 9-anthrylene group, a 1-phenanthrylene group, a 2-phenanthrylene group, a 3-phenanthrylene group, a 4-phenanthrylene group, and a 9-phenanthrylene group. Preferred are arylene groups having 6 to 14 carbon atoms, and more preferred are arylene groups having 6 to 10 carbon atoms.

The halogen atom generally indicates an atom of each of fluorine, chlorine, bromine, and iodine.

In the present invention, the ester linkage includes —COO— and —OCO—.

[Preparation of the Heterocyclic Compound Having a Dicyanostyryl Group]

The heterocyclic compound having a dicyanostyryl group may be obtained by the two methods described below.

(Synthesis Method 1 for the Heterocyclic Compound Having a Dicyanostyryl Group)

The heterocyclic compound having a dicyanostyryl group can be obtained by reacting an active proton compound having a dicyanostyryl group with a heterocyclic compound precursor having an epoxy group by a known method.

The active proton compound having a dicyanostyryl group is obtained by subjecting an active proton compound having a carbonyl group to cyanation. An example of the synthesis scheme is shown below.

Synthesis method for proton compound having a dicyanostryryl group

[Chemical formula 12]

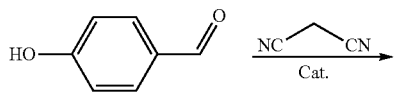

Active proton compound having a carbonyl group

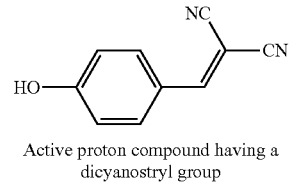

Active proton compound having a dicyanostryl group

An example of the synthesis scheme for reacting an active proton compound having a dicyanostyryl group with a heterocyclic compound precursor having an epoxy group is shown below.

Synthesis method 1 for heterocyclic compound having a dicyanostyryl group

[Chemical formula 13]

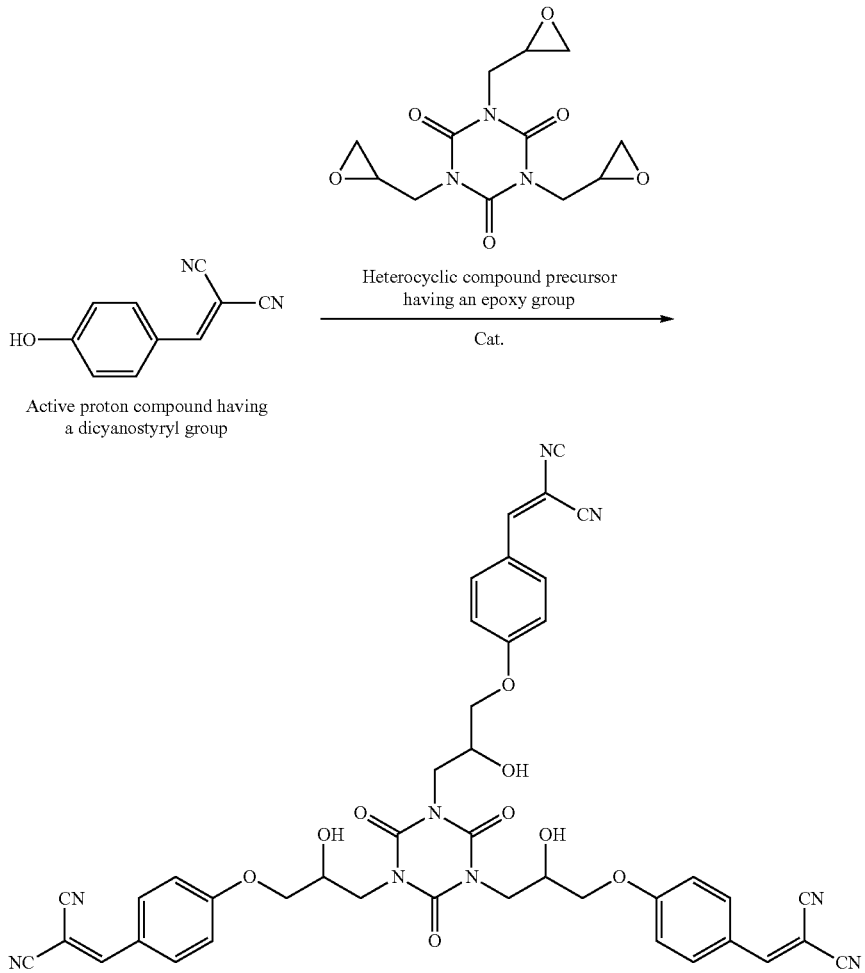

(Synthesis Method 2 for the Heterocyclic Compound Having a Dicyanostyryl Group)

The synthesis method comprises the steps of: reacting a heterocyclic compound precursor having an epoxy group with an active proton compound having a carbonyl group to obtain an intermediate compound; and subjecting the obtained intermediate compound to cyanation (dicyanation) according to, for example, the above-mentioned method. An example of the synthesis scheme is shown below.

Synthesis method 2 for heterocyclic compound having a dicyanostyryl group

[Chemical formula 14]

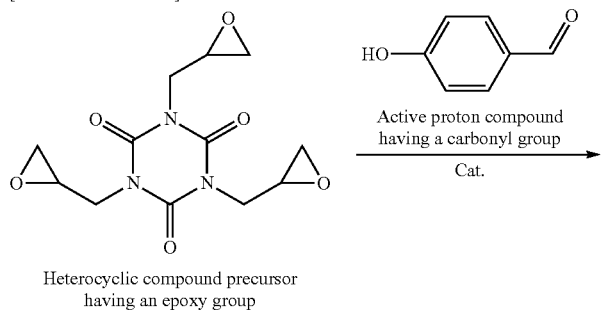

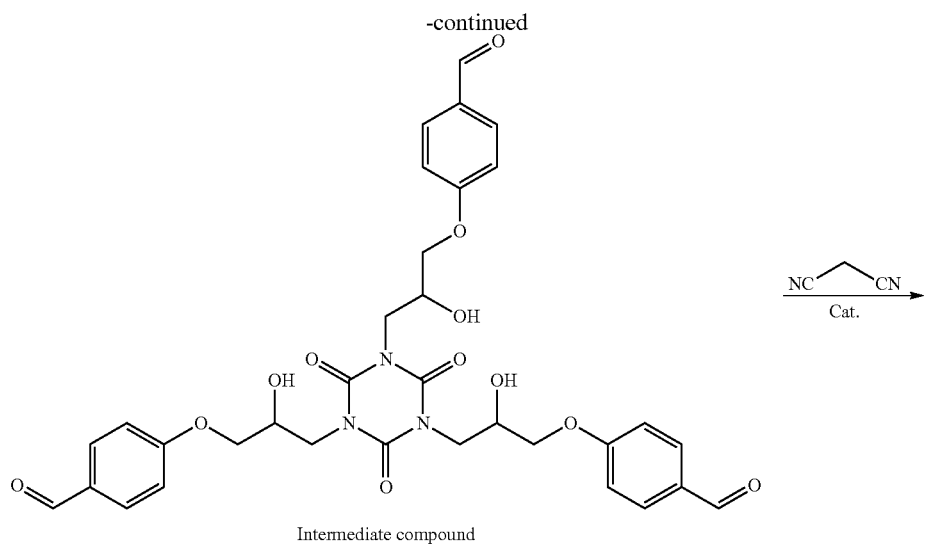
Intermediate compound
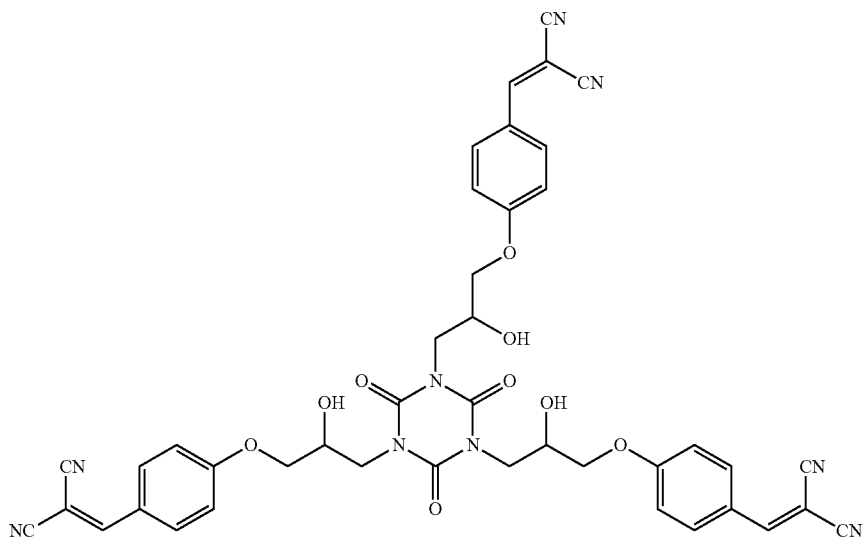
The heterocyclic compound precursor having an epoxy group in the present invention includes, for example, the following formulae (B-1) to (B-17), but the heterocyclic compound precursor is not limited to these formulae.
[Chemical formula 15]
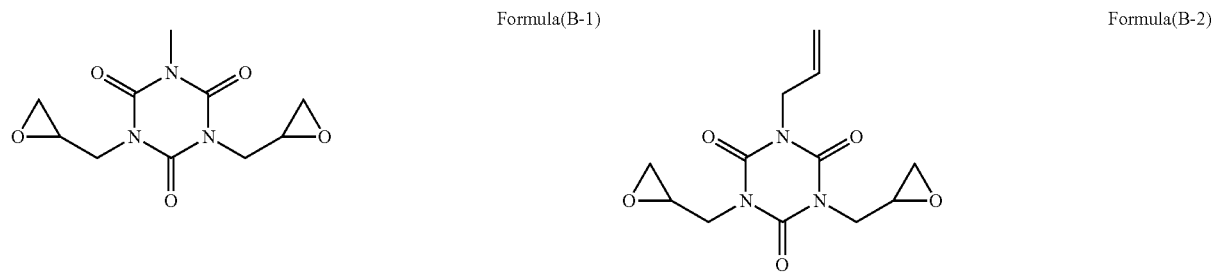
Formula(B-1)    Formula(B-2)

-continued
Formula(B-3)
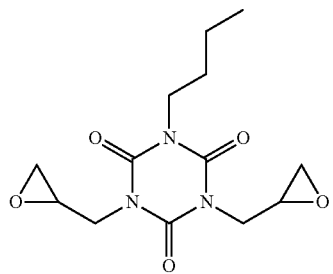
Formula(B-4)
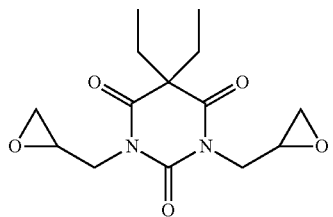
Formula(B-5)
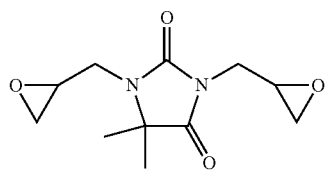
Formula(B-6)
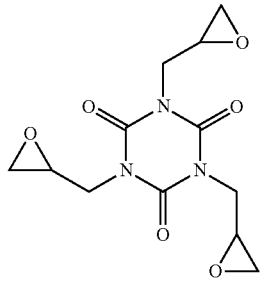
Formula(B-7)
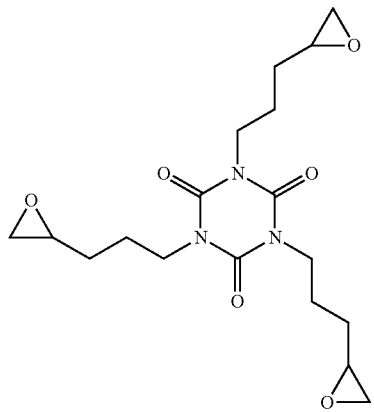
Formula(B-8)
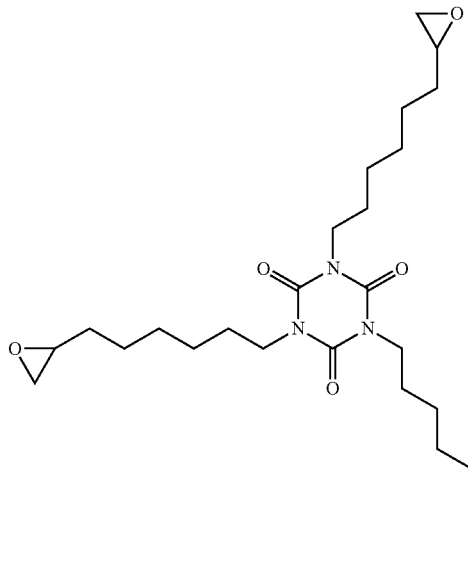
Formula(B-9)
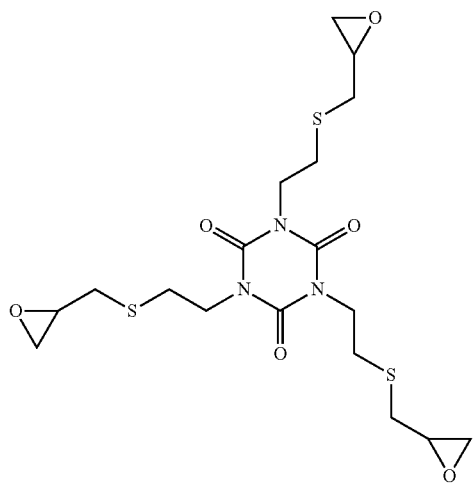

Formula(B-10)
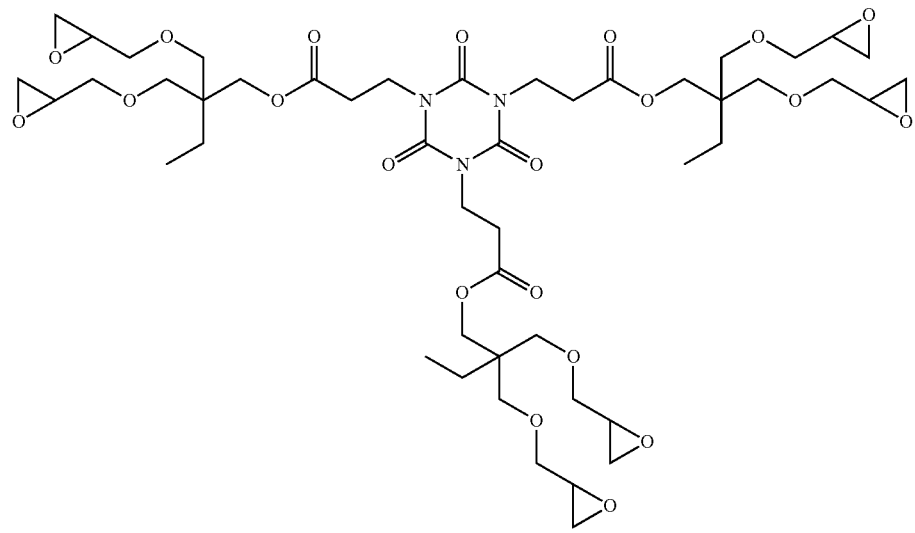
Formula(B-11)
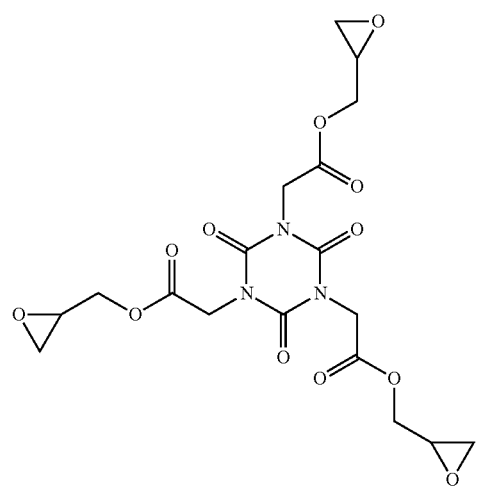
Formula(B-12)
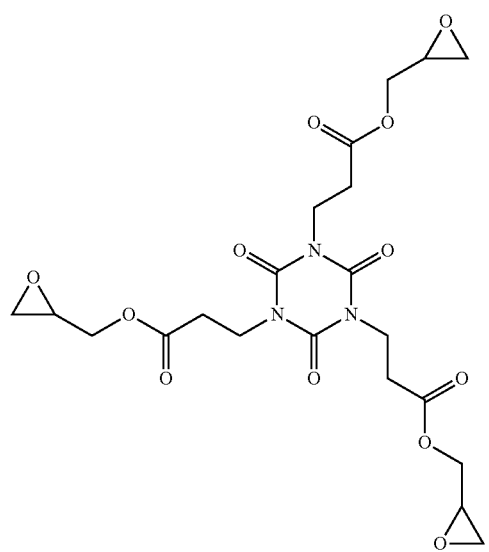

-continued
Formula(B-13)
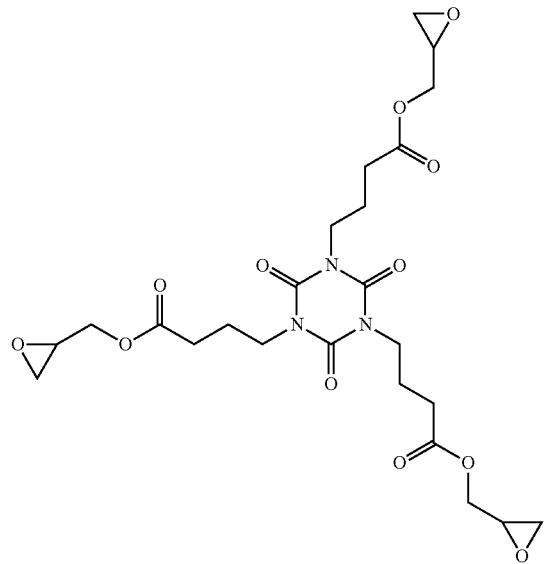
Formula(B-14)
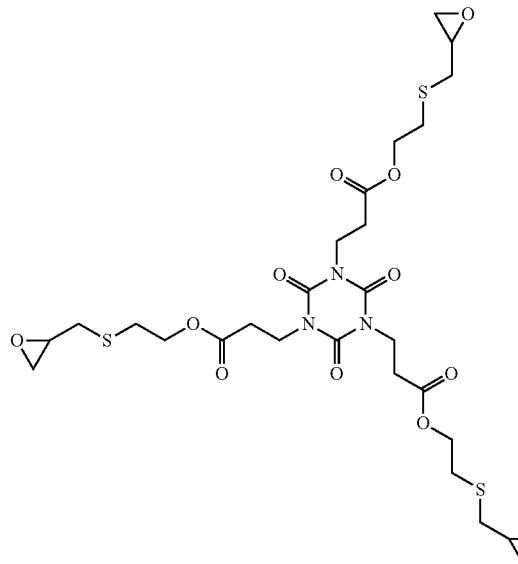
Formula(B-15)
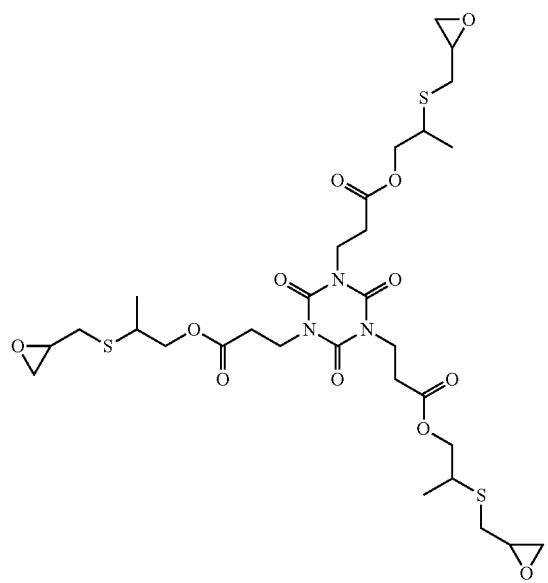
Formula(B-16)
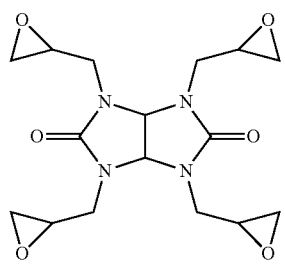
Formula(B-17)
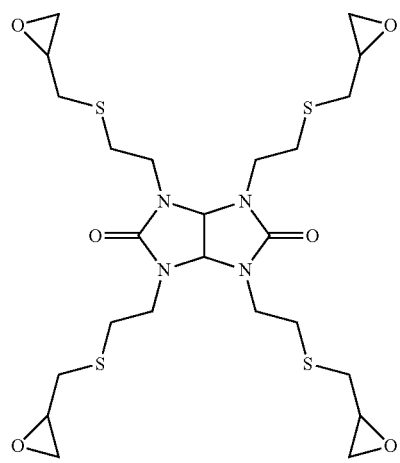

The active proton compound having a carbonyl group in the present invention includes, for example, the following formulae (C-1) to (C-40), but the compound is not limited to these formulae.

[Chemical formula 16-1]

Formula(C-1)

Formula(C-2)
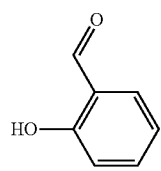

Formula(C-3)
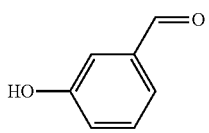

Formula(C-4)
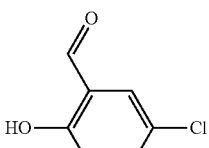

Formula(C-5)
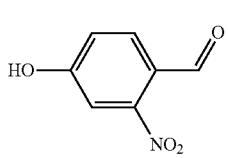

Formula(C-6)
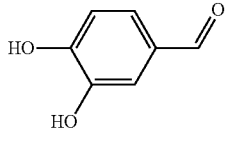

Formula(C-7)
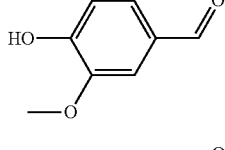

Formula(C-8)
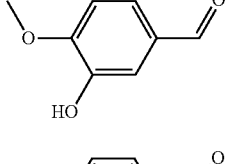

Formula(C-9)
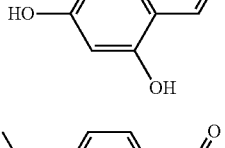

Formula(C-10)
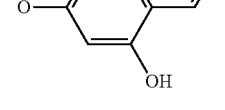

-continued

Formula(C-11)
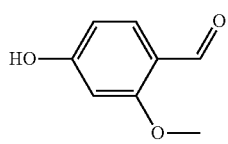

Formula(C-12)
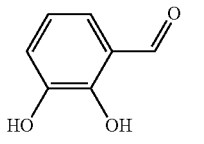

Formula(C-13)
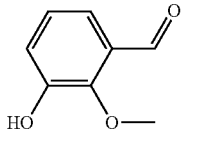

Formula(C-14)
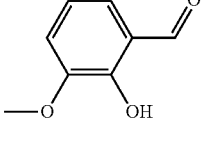

Formula(C-15)
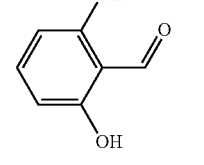

Formula(C-16)
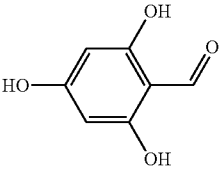

Formula(C-17)
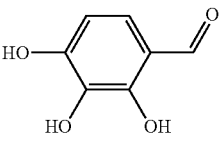

Formula(C-18)
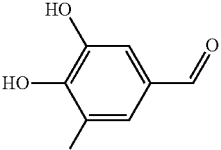

Formula(C-19)
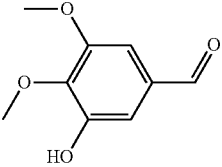

Formula(C-20)

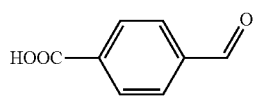
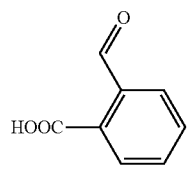
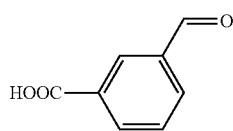
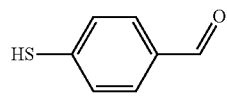

[Chemical formula 16-2]

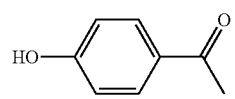
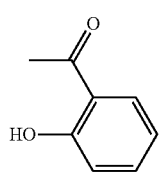
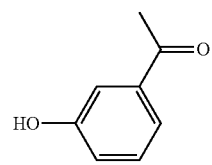
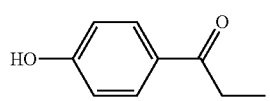
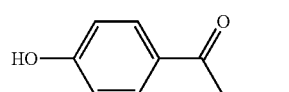
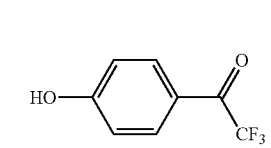
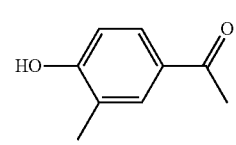

Formula(C-21)

Formula(C-22)

Formula(C-23)

Formula(C-24)

Formula(C-25)

Formula(C-26)

Formula(C-27)

Formula(C-28)

Formula(C-29)

Formula(C-30)

Formula(C-31)

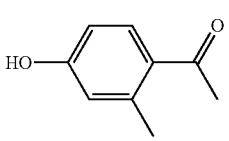 Formula(C-32)

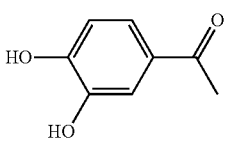 Formula(C-33)

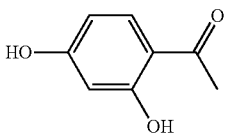 Formula(C-34)

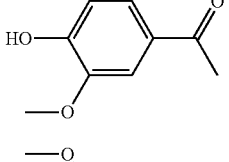 Formula(C-35)

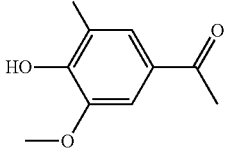 Formula(C-36)

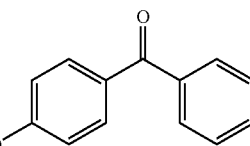 Formula(C-37)

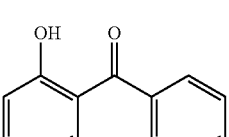 Formula(C-38)

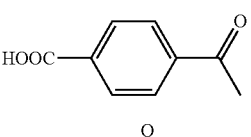 Formula(C-39)

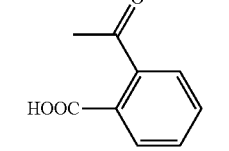 Formula(C-40)

Examples of catalysts used in the reaction for activating the epoxy group include quaternary phosphonium salts, such as ethyltriphenylphosphonium bromide and tetrabutylphosphonium bromide, and quaternary ammonium salts, such as benzyltriethylammonium chloride. The amount of the catalyst used is generally within the range of 0.001 to 1 equivalent, relative to 1 equivalent of the epoxy group.

The above-mentioned reaction may be conducted without using a solvent, but is generally conducted using a solvent. Any solvent may be used as long as it does not inhibit the reaction. Examples of solvents include ethers, such as 1,2- dimethoxyethane, diethylene glycol dimethyl ether, propylene glycol monomethyl ether, propylene glycol monomethyl ether acetate, tetrahydrofuran, and dioxane.

The reaction temperature is generally within the range of 40 to 200° C. The reaction time is appropriately selected depending on the reaction temperature, but is generally within the range of about 30 minutes to 50 hours.

The compound obtained as mentioned above generally has a weight average molecular weight Mw of 200 to 3,000, or 500 to 2,000.

[Solvent]

The solvent for the resist underlayer film-forming composition of the present invention is not particularly limited as long as it is a solvent which can dissolve therein the heterocyclic compound having a dicyanostyryl group and other components, and any of such solvents may be used. Particularly, the resist underlayer film-forming composition of the present invention is used in a uniform solution state, and therefore, taking the application properties of the composition into consideration, it is recommended that a solvent generally used in a lithography process should be also used.

Examples of such solvents include methyl cellosolve acetate, ethyl cellosolve acetate, propylene glycol, propylene glycol monomethyl ether, propylene glycol monoethyl ether, methylisobutyl carbinol, propylene glycol monobutyl ether, propylene glycol monomethyl ether acetate, propylene glycol monoethyl ether acetate, propylene glycol monopropyl ether acetate, propylene glycol monobutyl ether acetate, toluene, xylene, methyl ethyl ketone, cyclopentanone, cyclohexanone, ethyl 2-hydroxypropionate, ethyl 2-hydroxy-2-methylpropionate, ethyl ethoxyacetate, ethyl hydroxyacetate, methyl 2-hydroxy-3-methylbutanoate, methyl 3-methoxypropionate, ethyl 3-methoxypropionate, ethyl 3-ethoxypropionate, methyl 3-ethoxypropionate, methyl pyruvate, ethyl pyruvate, ethylene glycol monomethyl ether, ethylene glycol monoethyl ether, ethylene glycol monopropyl ether, ethylene glycol monobutyl ether, ethylene glycol monomethyl ether acetate, ethylene glycol monoethyl ether acetate, ethylene glycol monopropyl ether acetate, ethylene glycol monobutyl ether acetate, diethylene glycol dimethyl ether, diethylene glycol diethyl ether, diethylene glycol dipropyl ether, diethylene glycol dibutyl ether, propylene glycol monomethyl ether, propylene glycol dimethyl ether, propylene glycol diethyl ether, propylene glycol dipropyl ether, propylene glycol dibutyl ether, ethyl lactate, propyl lactate, isopropyl lactate, butyl lactate, isobutyl lactate, methyl formate, ethyl formate, propyl formate, isopropyl formate, butyl formate, isobutyl formate, amyl formate, isoamyl formate, methyl acetate, ethyl acetate, amyl acetate, isoamyl acetate, hexyl acetate, methyl propionate, ethyl propionate, propyl propionate, isopropyl propionate, butyl propionate, isobutyl propionate, methyl butyrate, ethyl butyrate, propyl butyrate, isopropyl butyrate, butyl butyrate, isobutyl butyrate, ethyl hydroxyacetate, ethyl 2-hydroxy-2-methylpropionate, methyl 3-methoxy-2-methylpropionate, methyl 2-hydroxy-3-methylbutyrate, ethyl methoxyacetate, ethyl ethoxyacetate, methyl 3-methoxypropionate, ethyl 3-ethoxypropionate, ethyl 3-methoxypropionate, 3-methoxybutyl acetate, 3-methoxypropyl acetate, 3-methyl-3-methoxybutyl acetate, 3-methyl-3-methoxybutyl propionate, 3-methyl-3-methoxybutyl butyrate, methyl acetoacetate, toluene, xylene, methyl ethyl ketone, methyl propyl ketone, methyl butyl ketone, 2-heptanone, 3-heptanone, 4-heptanone, cyclohexanone, N,N-dimethylformamide, N-methylacetamide, N,N-dimethylacetamide, N-methylpyrrolidone, 4-methyl-2-pentanol, and γ-butyrolactone. These solvents may be used each alone or in combination of two or more.

Preferred are, for example, propylene glycol monomethyl ether, propylene glycol monomethyl ether acetate, ethyl lactate, butyl lactate, and cyclohexanone. Especially preferred are propylene glycol monomethyl ether and propylene glycol monomethyl ether acetate.

[Crosslinking Agent Component]

The resist underlayer film-forming composition of the present invention may contain a crosslinking agent component. Examples of the crosslinking agents include melamines, substituted ureas, and polymers thereof. Preferred are crosslinking agents having at least two crosslink-forming substituents, and examples include compounds, such as methoxymethylated glycoluril (for example, tetramethoxymethylglycoluril), butoxymethylated glycoluril, methoxymethylated melamine, butoxymethylated melamine, methoxymethylated benzoguanamine, butoxymethylated benzoguanamine, methoxymethylated urea, butoxymethylated urea, and methoxymethylated thiourea. Further, condensation products of the above compound may be used.

As the crosslinking agent, a compound containing in the molecule thereof a crosslink-forming substituent having an aromatic ring (for example, a benzene ring or a naphthalene ring) may be used.

Examples of the compounds include compounds having a partial structure of formula (6) below, and polymers or oligomers having repeating units of formula (7) below.

[Chemical formula 17]

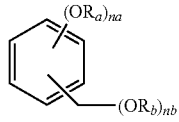

Formula (6)

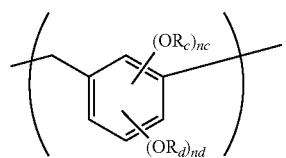

Formula (7)

The above-mentioned $R_a$, $R_b$, $R_c$, and $R_d$ are a hydrogen atom or an alkyl group having 1 to 10 carbon atoms, and each of na, nb, nc, and nd represents an integer of 0 to 3. As the alkyl group, those mentioned above as examples of alkyl groups may be used.

Examples of the compounds, polymers, and oligomers of formulae (6) and (7) are shown below.

[Chemical formula 18]

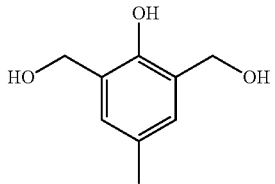

Formula(D-1)

Formula(D-2)
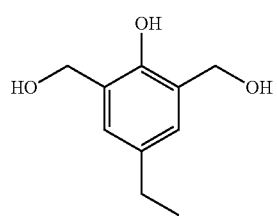
Formula(D-3)
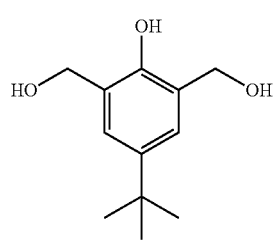
Formula(D-4)
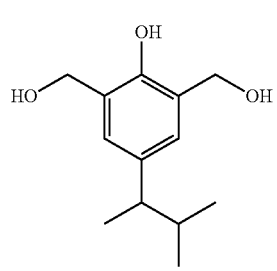
Formula(D-5)
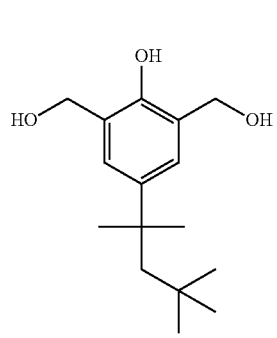
Formula(D-6)
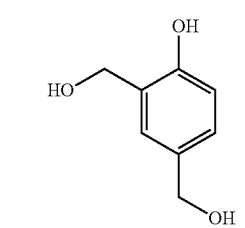
Formula(D-7)
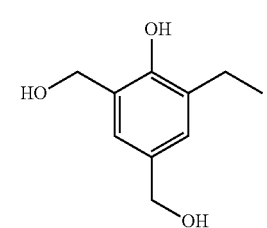
Formula(D-8)
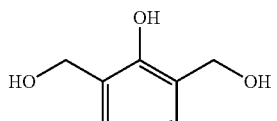
Formula(D-9)
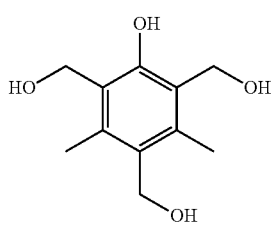
Formula(D-10)
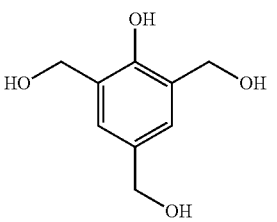
Formula(D-11)
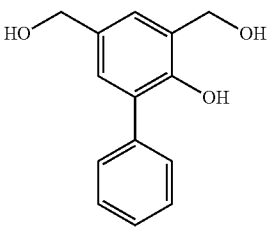
Formula(D-12)
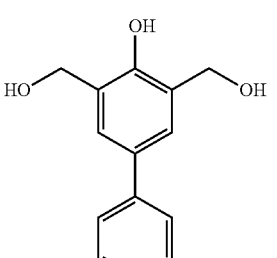
Formula(D-13)
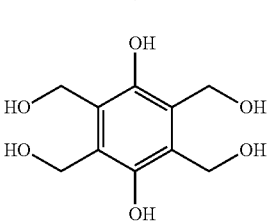
Formula(D-14)
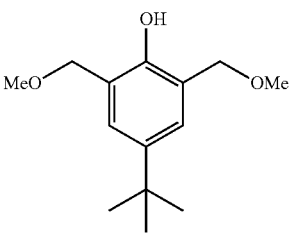

Formula(D-15)
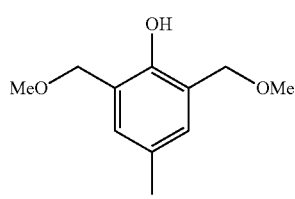

[Chemical formula 19]

Formula(D-16)
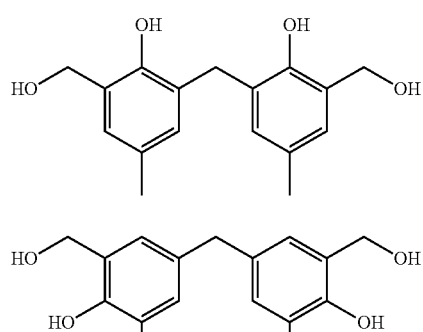

Formula(D-17)

Formula(D-18)
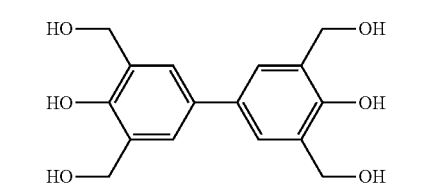

Formula(D-19)
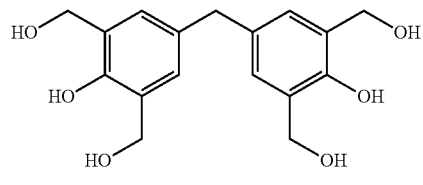

Formula(D-20)
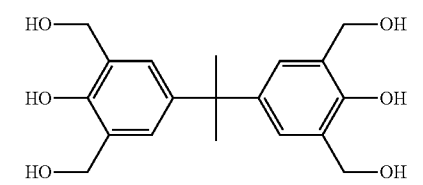

Formula(D-21)
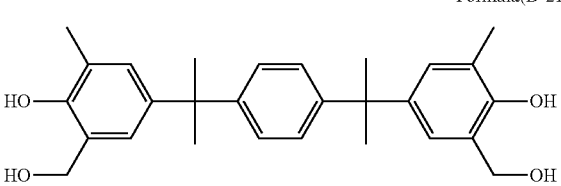

Formula(D-22)
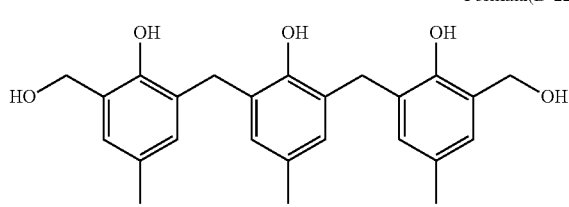

Formula(D-23)
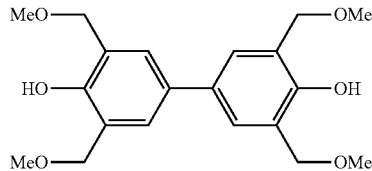

Formula(D-24)
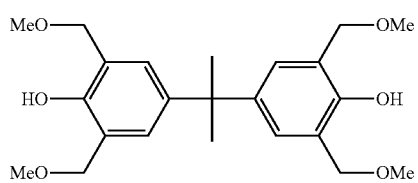

Formula(D-25)
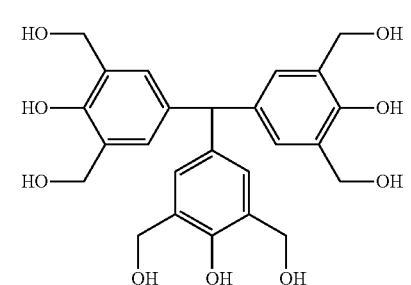

Formula(D-26)
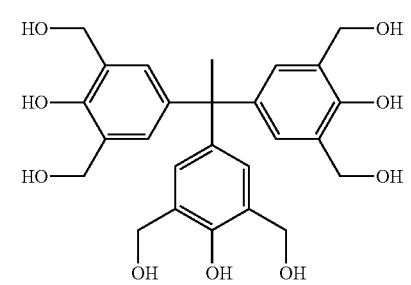

Formula(D-27)
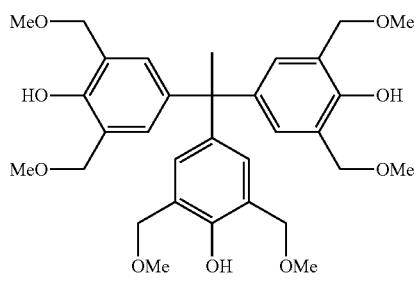

The above-mentioned compounds are available as products of Asahi Yukizai Corporation and Honshu Chemical Industry Co., Ltd. For example, of the above-mentioned crosslinking agents, the compound of formula (D-24) is available as trade name: TM-BIP-A, manufactured by Asahi Yukizai Corporation.

The amount of the crosslinking agent added varies depending on, for example, the application solvent used, the substrate used, the required solution viscosity, or the required film form; however, it is within the range of 0.001 to 80% by mass, preferably 0.01 to 50% by mass, further preferably 0.05 to 40% by mass, based on the mass of the solids of the resist underlayer film-forming composition. The crosslinking agent possibly causes a crosslinking reaction due to self-condensation. However, when the above-mentioned reaction product according to the present invention contains a crosslinkable substituent, a crosslinking reaction may occur between the crosslinking agent and the crosslinkable substituent.

[Acid and/or Acid Generator]

The resist underlayer film-forming composition of the present invention may contain an acid and/or an acid generator.

Examples of acids include p-toluenesulfonic acid, trifluoromethanesulfonic acid, pyridinium trifluoromethanesulfonate, pyridinium p-toluenesulfonate, pyridinium phenolsulfonate, salicylic acid, 5-sulfosalicylic acid, 4-phenolsulfonic acid, camphorsulfonic acid, 4-chlorobenzenesulfonic acid, benzenedisulfonic acid, 1-naphthalenesulfonic acid, citric acid, benzoic acid, hydroxybenzoic acid, and naphthalenecarboxylic acid.

The acids may be used each alone or in combination of two or more. The amount of the acid incorporated is generally within the range of 0.0001 to 20% by mass, preferably 0.0005 to 10% by mass, further preferably 0.01 to 3% by mass, based on the mass of the solids of the resist underlayer film-forming composition.

Examples of acid generators include a thermal acid generator and a photo-acid generator.

Examples of thermal acid generators include pyridinium trifluoromethanesulfonate, pyridinium p-toluenesulfonate, pyridinium phenolsulfonate, 2,4,4,6-tetrabromocyclohexadienone, benzoin tosylate, 2-nitrobenzyl tosylate, and other organic sulfonic acid alkyl esters.

The photo-acid generator generates an acid upon exposure for the resist. Therefore, it is possible to control the acidity of the resist underlayer film. This is a method of conforming the acidity of the resist underlayer film to the acidity of the resist as an upper layer. Further, the control of the acidity of the resist underlayer film enables control of the pattern form of the resist formed as an upper layer.

Examples of the photo-acid generators contained in the resist underlayer film-forming composition of the present invention include onium salt compounds, sulfonimide compounds, and disulfonyldiazomethane compounds.

Examples of onium salt compounds include iodonium salt compounds, such as diphenyliodonium hexafluorophosphate, diphenyliodonium trifluoromethanesulfonate, diphenyliodonium nonafluoronormalbutanesulfonate, diphenyliodonium perfluoronormaloctanesulfonate, diphenyliodonium camphorsulfonate, bis(4-tert-butylphenyl)iodonium camphorsulfonate, and bis(4-tert-butylphenyl)iodonium trifluoromethanesulfonate; and sulfonium salt compounds, such as triphenylsulfonium hexafluoroantimonate, triphenylsulfonium nonafluoronormalbutanesulfonate, triphenylsulfonium camphorsulfonate, and triphenylsulfonium trifluoromethanesulfonate.

Examples of succinimide compounds include N-(trifluoromethanesulfonyloxy)succinimide, N-(nonafluoronormalbutanesulfonyloxy)succinimide, N-(camphorsulfonyloxy)succinimide, and N-(trifluoromethanesulfonyloxy) naphthalimide.

Examples of disulfonyldiazomethane compounds include bis(trifluoromethylsulfonyl)diazomethane, bis(cyclohexylsulfonyl)diazomethane, bis(phenylsulfonyl)diazomethane, bis(p-toluenesulfonyl)diazomethane, bis(2,4-dimethylbenzenesulfonyl)diazomethane, and methylsulfonyl-p-toluenesulfonyldiazomethane.

The acid generators may be used each alone or in combination of two or more.

When an acid generator is used, the amount of the acid generator is generally within the range of 0.0001 to 20% by mass, preferably 0.0005 to 10% by mass, further preferably 0.01 to 3% by mass, relative to 100 parts by mass of the solids of the resist underlayer film-forming composition.

[Other Components]

In the resist underlayer film-forming composition of the present invention, for further improving the application properties to prevent the occurrence of pinhole or striation and uneven surface, a surfactant may be incorporated into the composition. Examples of surfactants include nonionic surfactants, e.g., polyoxyethylene alkyl ethers, such as polyoxyethylene lauryl ether, polyoxyethylene stearyl ether, polyoxyethylene cetyl ether, and polyoxyethylene oleyl ether; polyoxyethylene alkyl aryl ethers, such as polyoxyethylene octylphenol ether and polyoxyethylene nonylphenol ether; polyoxyethylene-polyoxypropylene block copolymers; sorbitan fatty acid esters, such as sorbitan monolaurate, sorbitan monopalmitate, sorbitan monostearate, sorbitan monooleate, sorbitan trioleate, and sorbitan tristearate; and polyoxyethylene sorbitan fatty acid esters, such as polyoxyethylene sorbitan monolaurate, polyoxyethylene sorbitan monopalmitate, polyoxyethylene sorbitan monostearate, polyoxyethylene sorbitan trioleate, and polyoxyethylene sorbitan tristearate, fluorine surfactants, such as EFTOP EF301, EF303, EF352 (trade name, manufactured by Tohchem Products Co., Ltd.), MEGAFACE F171, F173, R-40, R-40N, R-40LM (trade name, manufactured by DIC Corporation), Fluorad FC430, FC431 (trade name, manufactured by Sumitomo 3M), AsahiGuard AG710, Surflon S-382, SC101, SC102, SC103, SC104, SC105, SC106 (trade name, manufactured by AGC Inc.), and organosiloxane polymer KP341 (manufactured by Shin-Etsu Chemical Co., Ltd.). The amount of the surfactant incorporated is generally 2.0% by mass or less, preferably 1.0% by mass or less, based on the mass of the solids of the resist underlayer film material. These surfactants may be used each alone or in combination of two or more. When a surfactant is used, the amount of the surfactant is within the range of 0.0001 to 5 parts by mass, or 0.001 to 1 part by mass, or 0.01 to 0.5 part by mass, relative to 100 parts by mass of the solids of the resist underlayer film-forming composition.

In the resist underlayer film-forming composition of the present invention, for example, a light absorber, a rheology modifier, or a bonding auxiliary may be added. The rheology modifier is effective in improving the fluidity of the resist underlayer film-forming composition. The bonding auxiliary is effective in improving the adhesion between the resist underlayer film and a semiconductor substrate or a resist.

With respect to the light absorber, for example, a commercially available light absorber described in "Kougyo-you Shikiso no Gijutsu to Shijou (Techniques and Markets of Industrial Dyes)" (CMC Publishing Co., Ltd.) or "Senryo Binran (Dye Handbook)" (edited by The Society of Synthetic Organic Chemistry, Japan), for example, C. I. Disperse Yellow 1, 3, 4, 5, 7, 8, 13, 23, 31, 49, 50, 51, 54, 60, 64, 66, 68, 79, 82, 88, 90, 93, 102, 114, and 124; C. I. Disperse Orange 1, 5, 13, 25, 29, 30, 31, 44, 57, 72, and 73; C. I. Disperse Red 1, 5, 7, 13, 17, 19, 43, 50, 54, 58, 65, 72, 73, 88, 117, 137, 143, 199, and 210; C. I. Disperse Violet 43; C. I. Disperse Blue 96; C. I. Fluorescent Brightening Agent 112, 135, and 163; C. I. Solvent Orange 2 and 45; C. I. Solvent Red 1, 3, 8, 23, 24, 25, 27, and 49; C. I. Pigment Green 10; and C. I. Pigment Brown 2 may be preferably used. The light absorber is generally incorporated in an amount of 10% by mass or less, preferably 5% by mass or less, based on the mass of the solids of the resist underlayer film-forming composition.

A rheology modifier is added mainly for the purpose of improving the fluidity of the resist underlayer film-forming composition, particularly for improving the uniformity of the thickness of the resist underlayer film or the filling of the inside of hole with the resist underlayer film-forming composition in the baking step. Specific examples of rheology modifiers include phthalic acid derivatives, such as dimethyl phthalate, diethyl phthalate, diisobutyl phthalate, dihexyl phthalate, and butylisodecyl phthalate; adipic acid derivatives, such as dinormalbutyl adipate, diisobutyl adipate, diisooctyl adipate, and octyldecyl adipate; maleic acid derivatives, such as dinormalbutyl maleate, diethyl maleate, and dinonyl maleate; oleic acid derivatives, such as methyl oleate, butyl oleate, and tetrahydrofurfuryl oleate; and stearic acid derivatives, such as normalbutyl stearate and glyceryl stearate. The rheology modifier is generally incorporated in an amount of less than 30% by mass, based on the mass of the solids of the resist underlayer film-forming composition.

A bonding auxiliary is added mainly for the purpose of improving the adhesion between the resist underlayer film-forming composition and a substrate or a resist to prevent the resist from peeling off particularly in the development. Specific examples of bonding auxiliaries include chlorosilanes, such as trimethylchlorosilane, dimethylmethylolchlorosilane, methyldiphenylchlorosilane, and chloromethyldimethylchlorosilane; alkoxysilanes, such as trimethylmethoxysilane, dimethyldiethoxysilane, methyldimethoxysilane, dimethylmethylolethoxysilane, diphenyldimethoxysilane, and phenyltriethoxysilane; silazanes, such as hexamethyldisilazane, N,N'-bis(trimethylsilyl)urea, dimethyltrimethylsilylamine, and trimethylsilylimidazole; silanes, such as methyloltrichlorosilane, γ-chloropropyltrimethoxysilane, γ-aminopropyltriethoxysilane, and γ-glycidoxypropyltrimethoxysilane; heterocyclic compounds, such as benzotriazole, benzimidazole, indazole, imidazole, 2-mercaptobenzimidazole, 2-mercaptobenzothiazole, 2-mercaptobenzoxazole, urazole, thiouracil, mercaptoimidazole, and mercaptopyrimidine; and urea or thiourea compounds, such as 1,1-dimethylurea and 1,3-dimethylurea. The bonding auxiliary is generally incorporated in an amount of less than 5% by mass, preferably less than 2% by mass, based on the mass of the solids of the resist underlayer film-forming composition.

The resist underlayer film-forming composition of the present invention generally has a solid content of 0.1 to 70% by mass, preferably 0.1 to 60% by mass. The solid content indicates a content of the solids remaining after removing the solvent from the all components of the resist underlayer film-forming composition. The proportion of the above-mentioned reaction product in the solids is within the range of 1 to 100% by mass, 1 to 99.9% by mass, 50 to 99.9% by mass, 50 to 95% by mass, and 50 to 90% by mass, with increasing preference.

One measure for evaluating whether the resist underlayer film-forming composition is in a uniform solution state is to observe the passing property of the composition through a specific microfilter. The resist underlayer film-forming composition of the present invention can pass through a microfilter having a pore diameter of 0.1 μm and is in a uniform solution state.

Examples of materials for the microfilter include fluororesins, such as PTFE (polytetrafluoroethylene) and PFA (tetrafluoroethylene-perfluoroalkyl vinyl ether copolymer), PE (polyethylene), UPE (ultra-high molecular weight polyethylene), PP (polypropylene), PSF (polysulfone), PES (polyether sulfone), and nylon, and a microfilter made of PTFE (polytetrafluoroethylene) is preferred.

[Substrate]

In the present invention, examples of substrates used in the production of a semiconductor device include a silicon wafer substrate, a silicon/silicon dioxide coated substrate, a silicon nitride substrate, a glass substrate, an ITO substrate, a polyimide substrate, and a low permittivity material (low-k material) coated substrate.

Recently, in the field of three-dimensional mounting for semiconductor production process, for the purpose of reducing the length of a wiring between semiconductor chips to increase the response and save the power consumption, the application of a FOWLP process is spreading. In the RDL (redistribution layer) step for forming a wiring between semiconductor chips, copper (Cu) is used as a wiring member, and, as the copper wiring is becoming finer, the application of an antireflection film (resist underlayer film-forming composition) is needed. The resist underlayer film-forming composition of the present invention may be advantageously applied to a substrate having copper on the surface.

[Resist Underlayer Film and Method for Producing a Semiconductor Device]

Hereinbelow, the resist underlayer film using the resist underlayer film-forming composition of the present invention and the method for producing a semiconductor device are described.

The resist underlayer film-forming composition of the present invention is applied onto the above-mentioned substrate used in the production of a semiconductor device (for example, a substrate having copper on the surface) by an appropriate application method, such as a spinner or a coater, and then baked to form a resist underlayer film.

The conditions for baking are appropriately selected from those at a baking temperature of 80 to 400° C. for a baking time of 0.3 to 60 minutes. Preferred conditions for baking are those at a baking temperature of 150 to 350° C. for a baking time of 0.5 to 2 minutes. The thickness of the formed resist underlayer film is, for example, within the range of 10 to 1,000 nm, or 20 to 500 nm, or 30 to 400 nm, or 50 to 300 nm.

An inorganic resist underlayer film (hard mask) may be formed on the organic resist underlayer film of the present invention. For example, an inorganic resist underlayer film may be formed by spin coating the silicon-containing resist underlayer film (inorganic resist underlayer film) forming composition described in WO2009/104552A1, or a Si inorganic material film may be formed by, for example, a CVD method.

Then, a resist film, for example, a layer of photoresist is formed on the resist underlayer film. The layer of photoresist may be formed by a known method of removing a solvent from an applied film comprising the resist underlayer film-forming composition, namely, by applying a photoresist composition solution onto the resist underlayer film and baking the applied composition. The thickness of the photoresist is, for example, within the range of 50 to 10,000 nm, or 100 to 2,000 nm.

With respect to the photoresist formed on the resist underlayer film, there is no particular limitation as long as it is sensitive to a light used in the exposure. Any of a negative photoresist and a positive photoresist may be used. There are, for example, a positive photoresist comprising a novolak resin and 1,2-naphthoquinonediazidosulfonate; a chemical amplification photoresist comprising a photo-acid generator and a binder having a group that is decomposed due to an acid to increase the alkali solubility; a chemical amplification photoresist comprising an alkali-soluble binder, a photo-acid generator, and a low-molecular weight compound that is decomposed due to an acid to increase the alkali solubility of the photoresist; and a chemical amplification photoresist comprising a photo-acid generator, a binder having a group that is decomposed due to an acid to increase the alkali solubility, and a low-molecular weight compound that is decomposed due to an acid to increase the alkali solubility of the photoresist. Examples thereof include trade name: APEX-E, manufactured by Shipley Company, Inc., trade name: PAR710, manufactured by Sumitomo Chemical Co., Ltd., and trade name: SEPR430, manufactured by Shin-Etsu Chemical Co., Ltd. Further, they include fluorine atom-containing polymer photoresists described in, for example, Proc. SPIE, Vol. 3999, 330-334 (2000), Proc. SPIE, Vol. 3999, 357-364 (2000), and Proc. SPIE, Vol. 3999, 365-374 (2000).

Next, a resist pattern is formed by irradiation with a light or an electron beam and development. Exposure through a predetermined mask is first conducted. In the exposure, for example, a near ultraviolet light, a far ultraviolet light, or an extreme ultraviolet light (for example, an EUV (wavelength: 13.5 nm)) is used. Specifically, for example, an i-line (wavelength: 365 nm), a KrF excimer laser (wavelength: 248 nm), an ArF excimer laser (wavelength: 193 nm), or an $F_2$ excimer laser (wavelength: 157 nm) may be used. Of these, an i-line (wavelength: 365 nm) is preferred. After the exposure, if necessary, post exposure bake may be performed. The post exposure bake is performed under conditions appropriately selected from those at a heating temperature of 70 to 150° C. for a heating time of 0.3 to 10 minutes.

Further, in the present invention, as a resist, instead of the photoresist, a resist for electron beam lithography may be used. Any of a negative electron beam resist and a positive electron beam resist may be used. There are, for example, a chemical amplification resist comprising an acid generator and a binder having a group that is decomposed due to an acid to change the alkali solubility; a chemical amplification resist comprising an alkali-soluble binder, an acid generator, and a low-molecular weight compound that is decomposed due to an acid to change the alkali solubility of the resist; a chemical amplification resist comprising an acid generator, a binder having a group that is decomposed due to an acid to change the alkali solubility, and a low-molecular weight compound that is decomposed due to an acid to change the alkali solubility of the resist; a non-chemical amplification resist comprising a binder having a group that is decomposed due to an electron beam to change the alkali solubility; and a non-chemical amplification resist comprising a binder having a site that suffers breakage due to an electron beam to change the alkali solubility. Also when using the above electron beam resist, a resist pattern may be similarly formed as in the case where a photoresist is used and an electron beam is used as a source of irradiation.

Then, development using a developer is conducted. In the development, for example, when a positive photoresist is used, the exposed portion of the photoresist is removed, so that a photoresist pattern is formed.

Examples of developers include alkaline aqueous solutions, e.g., aqueous solutions of an alkali metal hydroxide, such as potassium hydroxide or sodium hydroxide, aqueous solutions of a quaternary ammonium hydroxide, such as tetramethylammonium hydroxide, tetraethylammonium hydroxide, or choline, and aqueous solutions of an amine, such as ethanolamine, propylamine, or ethylenediamine. Further, for example, a surfactant may be added to the above developer. The conditions for the development are appropriately selected from those at a temperature of 5 to 50° C. for a time of 10 to 600 seconds.

In the present invention, an organic underlayer film (lower layer) is formed on a substrate, and then an inorganic underlayer film (intermediate layer) is formed on the organic underlayer film, and the resultant film may be covered with a photoresist (upper layer). By virtue of this, even when a substrate is covered with a photoresist having a smaller thickness for preventing an occurrence of pattern collapse due to a reduced pattern width of the photoresist, appropriate selection of an etching gas enables processing of the substrate. For example, processing of the resist underlayer film may be made by using as an etching gas a fluorine-based gas having an etching rate that is satisfactorily faster than that for the photoresist, and processing of the substrate may be made by using as an etching gas a fluorine-based gas having an etching rate that is satisfactorily faster than that for the inorganic underlayer film, and further processing of the substrate may be made by using as an etching gas an oxygen-based gas having an etching rate that is satisfactorily faster than that for the organic underlayer film.

Subsequently, using the thus formed photoresist pattern as a protective film, the inorganic underlayer film is removed, and then, using a film comprising the patterned photoresist and inorganic underlayer film as a protective film, the organic underlayer film is removed. Finally, using the patterned inorganic underlayer film and organic underlayer film as a protective film, processing of the semiconductor substrate is performed.

First, a portion of the inorganic underlayer film, from which the photoresist has been removed, is removed by dry etching so as to expose the semiconductor substrate. In the dry etching for the inorganic underlayer film, for example, a gas of tetrafluoromethane ($CF_4$), perfluorocyclobutane ($C_4F_8$), perfluoropropane (CSFs), trifluoromethane, carbon monoxide, argon, oxygen, nitrogen, sulfur hexafluoride, difluoromethane, nitrogen trifluoride, chlorine trifluoride, chlorine, trichloroborane, or dichloroborane can be used. In the dry etching for the inorganic underlayer film, a halogen-based gas is preferably used, and a fluorine-based gas is more preferably used. Examples of fluorine-based gases include tetrafluoromethane ($CF_4$), perfluorocyclobutane ($C_4F_8$), perfluoropropane ($C_3F_8$), trifluoromethane, and difluoromethane ($CH_2F_2$).

Then, using a film comprising the patterned photoresist and inorganic underlayer film as a protective film, the organic underlayer film is removed.

The inorganic underlayer film containing silicon atoms in a large amount is unlikely to be removed by dry etching using an oxygen-based gas, and therefore the organic underlayer film is often removed by dry etching using an oxygen-based gas.

Finally, processing of the semiconductor substrate is conducted. The processing of the semiconductor substrate is preferably conducted by dry etching using a fluorine-based gas.

Examples of fluorine-based gases include tetrafluoromethane ($CF_4$), perfluorocyclobutane ($C_4F_8$), perfluoropropane ($C_3F_8$), trifluoromethane, and difluoromethane ($CH_2F_2$).

Further, before forming the photoresist, an organic antireflection film may be formed on the resist underlayer film as an upper layer. With respect to the antireflection film composition used in forming the antireflection film, there is no particular limitation. Any antireflection film composition may be selected from those which have been commonly used in a lithography process. An antireflection film may be formed by a method commonly used, for example, by applying the composition using a spinner or a coater and baking it.

The resist underlayer film formed from the resist underlayer film-forming composition may have an absorption to the light used in a lithography process, depending on the wavelength of the light. In such a case, the resist underlayer film may function as an antireflection film having an effect of preventing a light reflected from the substrate. Further, the resist underlayer film formed from the resist underlayer film-forming composition of the present invention may function as a hard mask. The resist underlayer film of the present invention may also be used as, for example, a layer for preventing an interaction between a substrate and a photoresist, a layer having a function that it prevents an adverse effect on a substrate of the material used in a photoresist or a substance formed during the exposure for the photoresist, a layer having a function that it prevents a substance generated from a substrate upon heating or baking from diffusing into a photoresist as an upper layer, and a barrier layer for reducing the photoresist layer poisoning effect of a semiconductor substrate dielectric layer.

Further, the resist underlayer film formed from the resist underlayer film-forming composition is applied to a substrate having formed via holes used in a dual-damascene process, and may be used as an encapsulation material capable of completely filling holes. Furthermore, the resist underlayer film may also be used as a planarization material for making the uneven surface of a semiconductor substrate flat.

Meanwhile, for the purpose of simplifying the steps for process, reducing a damage to the substrate, and reducing the cost, a method of removing the resist underlayer film by wet etching using a chemical liquid, instead of dry etching, has been studied. However, with respect to the resist underlayer film formed from a conventional resist underlayer film-forming composition, for suppressing mixing of the resist underlayer film and the resist being applied, it is necessary that the cured film obtained from the resist underlayer film-forming composition inherently have a solvent resistance. Further, the resist underlayer film must have a resistance to a developer necessarily used to develop the resist when patterning the resist. Therefore, it is difficult for the conventional technique to achieve such a resist underlayer film-forming composition that the cured film obtained from the composition is insoluble in a resist solvent and a developer and soluble only in a wet etching liquid. However, the resist underlayer film-forming composition of the present invention can provide a resist underlayer film which can be etched (removed) by a wet etching liquid.

The wet etching liquid preferably contains, for example, an organic solvent, and may contain an acidic compound or a basic compound. Examples of organic solvents include dimethyl sulfoxide, dimethylformamide, dimethylacetamide, N-methylpyrrolidone, N-ethylpyrrolidone, ethylene glycol, propylene glycol, and diethylene glycol dimethyl ether. Examples of acidic compounds include inorganic acids and organic acids, and examples of inorganic acids include hydrochloric acid, sulfuric acid, nitric acid, and phosphoric acid, and examples of organic acids include p-toluenesulfonic acid, trifluoromethanesulfonic acid, salicylic acid, 5-sulfosalicylic acid, 4-phenolsulfonic acid, camphorsulfonic acid, 4-chlorobenzenesulfonic acid, benzenedisulfonic acid, 1-naphthalenesulfonic acid, acetic acid, propionic acid, trifluoroacetic acid, citric acid, benzoic acid, hydroxybenzoic acid, and naphthalenecarboxylic acid. Examples of basic compounds include inorganic bases and organic bases, and examples of inorganic bases include alkali metal hydroxides, such as sodium hydroxide and potassium hydroxide, quaternary ammonium hydroxides, such as tetramethylammonium hydroxide, tetraethylammonium hydroxide, and choline, and amines, such as ethanolamine, propylamine, diethylaminoethanol, and ethylenediamine. In the wet etching liquid, only one type of an organic solvent may be used, or two or more types of organic solvents may be used in combination. Further, only one type of an acidic compound or basic compound may be used, or two or more types of acidic compounds or basic compounds may be used in combination. The amount of the acidic compound or basic compound incorporated is within the range of 0.01 to 20% by weight, preferably 0.1 to 5% by weight, especially preferably 0.2 to 1% by weight, based on the weight of the wet etching liquid. With respect to the wet etching liquid, preferred is an organic solvent containing a basic compound, and especially preferred is a mixture containing dimethyl sulfoxide and tetramethylammonium hydroxide.

Recently, in the field of three-dimensional mounting for semiconductor production process, the application of a FOWLP (Fan-Out Wafer Level Package) process is spreading, and, in the RDL (redistribution layer) step for forming a copper wiring, a resist underlayer film may be applied.

The resist underlayer film used in a representative RDL step is described below, but is not limited to the description. A photosensitive insulating film is first formed on a semiconductor chip, and then subjected to patterning by irradiation with a light (exposure) and development so that a semiconductor chip electrode portion is opened. Subsequently, a copper seed layer for forming a copper wiring as a wiring member in the plating step is formed by sputtering. Then, a resist underlayer film and a photoresist layer are successively formed, and then subjected to irradiation with a light and development to perform patterning of the resist. The unnecessary resist underlayer film is removed by dry etching, and the exposed copper seed layer in the resist pattern is subjected to copper electroplating to form a copper wiring constituting a first wiring layer. Further, the unnecessary resist, resist underlayer film, and copper seed layer are removed by dry etching or wet etching or both of them. The formed copper wiring layer is further coated with an insulating film, and then a copper seed layer, a resist underlayer film, and a resist are formed in this order, and patterning of the resist, removal of the resist underlayer film, and copper plating are conducted to form a second copper wiring layer. The above steps are repeated to form an intended copper wiring, and then a bump for taking out an electrode is formed.

The resist underlayer film-forming composition of the present invention is advantageous in that the resist underlayer film obtained from the composition can be removed by wet etching, and therefore, from the viewpoint of simplifying the steps for process and reducing a damage to the processed substrate, the resist underlayer film-forming composition of the present invention can be especially advantageously used for a resist underlayer film in the RDL step.

EXAMPLES

Hereinbelow, the present invention will be described in detail with reference to the following Examples, which should not be construed as limiting the scope of the present invention.

The apparatus and other conditions used in the measurement of the weight average molecular weight of the polymers obtained in the following Synthesis Examples are shown below.

Apparatus: HLC-8320GPC, manufactured by Tosoh Corp.

GPC Column: Shodex [registered trademark]-Asahipak [registered trademark] (Showa Denko K.K.)

Column temperature: 40° C.
Flow rate: 0.35 mL/minute
Eluent: Tetrahydrofuran (THF)
Standard sample: Polystyrene (Tosoh Corp.)

Synthesis Example 1

10.00 g of a triazine epoxy compound (product name: TEPIC, manufactured by Nissan Chemical Corporation; epoxy functionality: 10.03 eq./kg), 12.25 g of 4-hydroxybenzaldehyde, 0.85 g of tetrabutylphosphonium bromide, and 53.90 g of propylene glycol monomethyl ether were placed in a reaction flask and heated under reflux in a nitrogen gas atmosphere for 23 hours. Subsequently, a solution prepared by dissolving 6.63 g of malononitrile in 15.46 g of propylene glycol monomethyl ether was added to the system, and the resultant mixture was further heated under reflux for 5 hours. The obtained reaction product, which corresponds to formula (A-1), had a weight average molecular weight Mw of 800, as determined by GPC using a conversion calibration curve obtained from the standard polystyrene.

[Chemical formula 20]

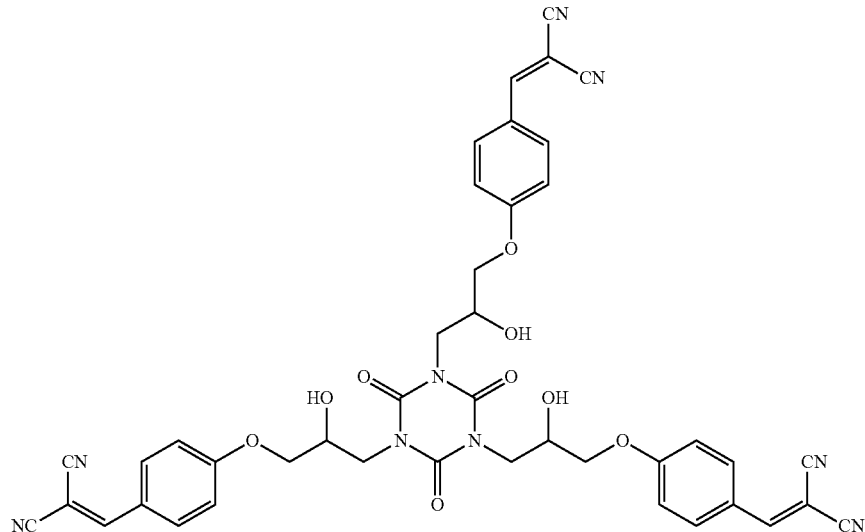

Formula (A-1)

Synthesis Example 2

9.00 g of a triazine epoxy compound (product name: TEPIC, manufactured by Nissan Chemical Corporation; epoxy functionality: 10.03 eq./kg), 5.51 g of 4-hydroxybenzaldehyde, 6.78 g of terephthalaldehydic acid, 1.53 g of tetrabutylphosphonium bromide, and 34.23 g of propylene glycol monomethyl ether were placed in a reaction flask and heated under reflux in a nitrogen gas atmosphere for 23 hours. Subsequently, a solution prepared by dissolving 5.96 g of malononitrile in 32.93 g of propylene glycol monomethyl ether was added to the system, and the resultant mixture was further heated under reflux for 4 hours. The obtained reaction product, which corresponds to formula (A-2), had a weight average molecular weight Mw of 900, as determined by GPC using a conversion calibration curve obtained from the standard polystyrene.

[Chemical formula 21]

Formula (A-2)

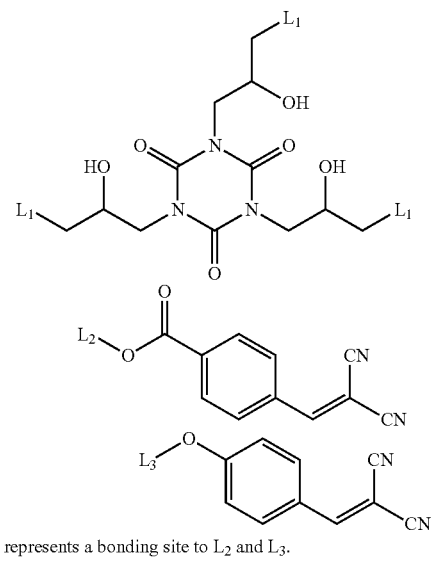

$L_1$ represents a bonding site to $L_2$ and $L_3$.

Comparative Synthesis Example 1

15.00 g of a phenolic novolak epoxy resin (product name: DEN, manufactured by The Dow Chemical Company; epoxy functionality: 5.55 eq./kg), 10.17 g of 4-hydroxybenzaldehyde, 1.41 g of tetrabutylphosphonium bromide, and 39.87 g of propylene glycol monomethyl ether were placed in a reaction flask and heated under reflux in a nitrogen gas atmosphere for 24 hours. Subsequently, a solution prepared by dissolving 5.50 g of malononitrile in 34.99 g of propylene glycol monomethyl ether was added to the system, and the resultant mixture was further heated under reflux for 4 hours. The obtained reaction product, which corresponds to formula (A-3), had a weight average molecular weight Mw of 2,100, as determined by GPC using a conversion calibration curve obtained from the standard polystyrene.

[Chemical formula 22]

Formula (A-3)

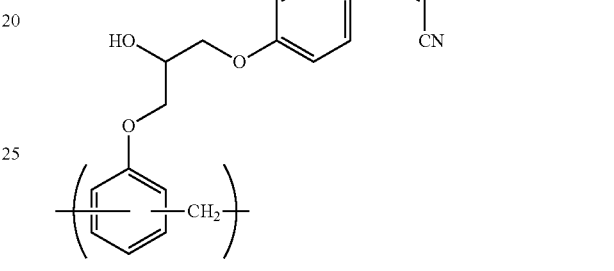

Comparative Synthesis Example 2

12.00 g of a phenolic novolak epoxy resin (product name: DEN, manufactured by The Dow Chemical Company; epoxy functionality: 5.55 eq./kg), 4.07 g of 4-hydroxybenzaldehyde, 5.00 g of terephthalaldehydic acid, 1.13 g of tetrabutylphosphonium bromide, and 33.30 g of propylene glycol monomethyl ether were placed in a reaction flask and heated under reflux in a nitrogen gas atmosphere for 23 hours. Subsequently, a solution prepared by dissolving 4.40 g of malononitrile in 28.77 g of propylene glycol monomethyl ether was added to the system, and the resultant mixture was further heated under reflux for 4 hours. The obtained reaction product, which corresponds to formula (A-4), had a weight average molecular weight Mw of 2,400, as determined by GPC using a conversion calibration curve obtained from the standard polystyrene.

[Chemical formula 23]

Formula (A-4)

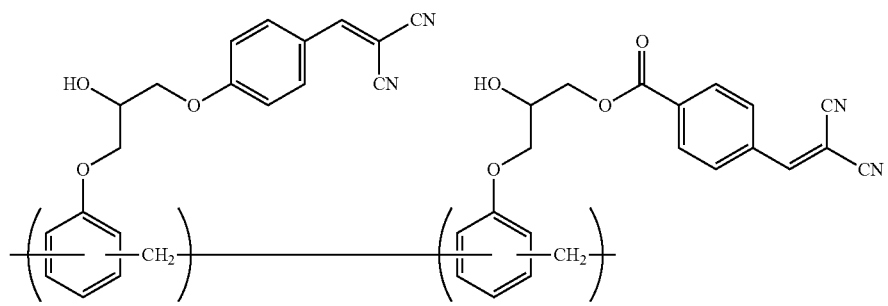

Comparative Synthesis Example 3

12.00 g of a cyclohexane epoxy resin (product name: EHPE3150, manufactured by Daicel Corporation; epoxy functionality: 5.99 eq./kg), 4.39 g of 4-hydroxybenzaldehyde, 5.40 g of terephthalaldehydic acid, 1.22 g of tetrabutylphosphonium bromide, and 34.50 g of propylene glycol monomethyl ether were placed in a reaction flask and heated under reflux in a nitrogen gas atmosphere for 23 hours. Further, a solution prepared by dissolving 4.75 g of malononitrile in 30.25 g of propylene glycol monomethyl ether was added to the system, and then the resultant mixture was heated under reflux for 4 hours. The obtained reaction product, which corresponds to formula (A-5), had a weight average molecular weight Mw of 5,400, as determined by GPC using a conversion calibration curve obtained from the standard polystyrene.

[Chemical formula 24]

Formula (A-5)

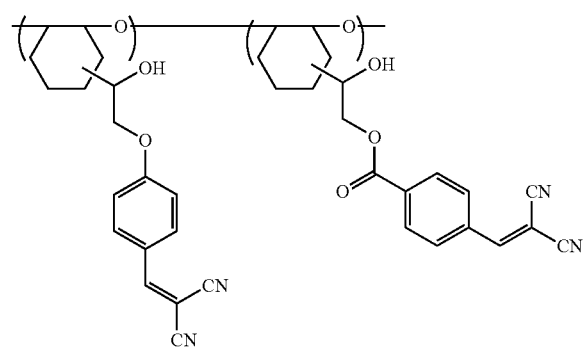

Example 1

To 6.72 g of the solution of the reaction product, which corresponds to formula (A-1) above (having a solid content of 25.8% by weight), were added 0.35 g of tetramethoxymethylglycoluril as a crosslinking agent, 0.02 g of pyridinium p-toluenesulfonate as a crosslinking catalyst, 14.54 g of propylene glycol monomethyl ether, and 8.37 g of propylene glycol monomethyl ether acetate, to prepare a resist underlayer film-forming composition in the form of a solution.

Example 2

To 7.56 g of the solution of the reaction product, which corresponds to formula (A-2) above (having a solid content of 23.9% by weight), were added 0.27 g of tetramethoxymethylglycoluril as a crosslinking agent, 0.02 g of pyridinium p-toluenesulfonate as a crosslinking catalyst, 13.78 g of propylene glycol monomethyl ether, and 8.37 g of propylene glycol monomethyl ether acetate, to prepare a resist underlayer film-forming composition in the form of a solution.

Example 3

To 6.96 g of the solution of the reaction product, which corresponds to formula (A-2) above (having a solid content of 23.9% by weight), were added 0.42 g of 3,3',5,5'-tetrakis(methoxymethyl)-4,4'-dihydroxybiphenyl (product name: TMOM-BP, manufactured by Honshu Chemical Industry Co., Ltd.) as a crosslinking agent, 0.02 g of pyridinium p-toluenesulfonate as a crosslinking catalyst, 14.23 g of propylene glycol monomethyl ether, and 8.37 g of propylene glycol monomethyl ether acetate, to prepare a resist underlayer film-forming composition in the form of a solution.

Example 4

To 8.20 g of the solution of the reaction product, which corresponds to formula (A-2) above (having a solid content of 23.9% by weight), were added 0.14 g of pyridinium trifluoromethanesulfonate as a crosslinking catalyst, 13.29 g of propylene glycol monomethyl ether, and 8.37 g of propylene glycol monomethyl ether acetate, to prepare a resist underlayer film-forming composition in the form of a solution.

Comparative Example 1

To 7.58 g of the solution of the reaction product, which corresponds to formula (A-3) above (having a solid content of 22.9% by weight), were added 0.35 g of tetramethoxymethylglycoluril as a crosslinking agent, 0.02 g of pyridinium p-toluenesulfonate as a crosslinking catalyst, 13.69 g of propylene glycol monomethyl ether, and 8.37 g of propylene glycol monomethyl ether acetate, to prepare a resist underlayer film-forming composition in the form of a solution.

Comparative Example 2

To 7.98 g of the solution of the reaction product, which corresponds to formula (A-4) above (having a solid content of 22.7% by weight), were added 0.27 g of tetramethoxymethylglycoluril as a crosslinking agent, 0.02 g of pyridinium p-toluenesulfonate as a crosslinking catalyst, 13.36 g of propylene glycol monomethyl ether, and 8.37 g of propylene glycol monomethyl ether acetate, to prepare a resist underlayer film-forming composition in the form of a solution.

Comparative Example 3

To 7.35 g of the solution of the reaction product, which corresponds to formula (A-4) above (having a solid content of 22.7% by weight), were added 0.42 g of 3,3',5,5'-tetrakis(methoxymethyl)-4,4'-dihydroxybiphenyl (product name: TMOM-BP, manufactured by Honshu Chemical Industry Co., Ltd.) as a crosslinking agent, 0.02 g of pyridinium p-toluenesulfonate as a crosslinking catalyst, 13.85 g of propylene glycol monomethyl ether, and 8.37 g of propylene glycol monomethyl ether acetate, to prepare a resist underlayer film-forming composition in the form of a solution.

Comparative Example 4

To 8.81 g of the solution of the reaction product, which corresponds to formula (A-4) above (having a solid content of 22.7% by weight), were added 0.10 g of pyridinium trifluoromethanesulfonate as a crosslinking catalyst, 12.72 g of propylene glycol monomethyl ether, and 8.37 g of propylene glycol monomethyl ether acetate, to prepare a resist underlayer film-forming composition in the form of a solution.

Comparative Example 5

To 8.12 g of the solution of the reaction product, which corresponds to formula (A-5) above (having a solid content of 22.3% by weight), were added 0.27 g of tetramethoxymethylglycoluril as a crosslinking agent, 0.02 g of pyridinium p-toluenesulfonate as a crosslinking catalyst, 13.22 g of propylene glycol monomethyl ether, and 8.37 g of propylene glycol monomethyl ether acetate, to prepare a resist underlayer film-forming composition in the form of a solution.

[Evaluation of Optical Coefficient]

Evaluation of optical coefficient was made as follows. Each of the resist underlayer film-forming compositions for lithography prepared in Examples 1 to 4 was applied onto a silicon wafer using a spin coater so that the resultant film had a thickness of about 50 nm, and baked on a hotplate at 200° C. for 90 seconds. The n value (refractive index) and k value (attenuation coefficient) at a wavelength of 193 nm (ArF excimer laser wavelength), 248 nm (KrF excimer laser wavelength), and 365 nm (i-line wavelength) of the obtained resist underlayer film were determined using a spectroscopic ellipsometer (VUV-VASE, manufactured by J. A. Woolam Co., Inc.). The results are shown in Table 1.

TABLE 1

| Example | n/k (193 nm) | n/k (248 nm) | n/k (365 nm) |
|---|---|---|---|
| Example 1 | 1.83/0.38 | 1.64/0.16 | 1.91/0.47 |
| Example 2 | 1.78/0.41 | 1.61/0.11 | 1.83/0.23 |
| Example 3 | 1.71/0.44 | 1.63/0.12 | 1.83/0.21 |
| Example 4 | 1.78/0.44 | 1.61/0.12 | 1.83/0.23 |

In Examples 1 to 4, the resist underlayer films had an appropriate n value and k value at 193 nm, 248 nm, and 365 nm. As apparent from the above results, the film obtained from each of the resist underlayer film-forming compositions obtained in Examples 1 to 4 has an antireflection function such that the film can suppress the reflection (standing wave) from the substrate, in which the reflection causes an unfavorable resist pattern in the lithography process using such a radiation as an ArF excimer laser, a KrF excimer laser, and an i-line. Therefore, the film is useful as a resist underlayer film.

[Evaluation of Etching Selective Ratio]

Evaluation of etching selective ratio was made as follows. Each of the resist underlayer film-forming compositions for lithography prepared in Examples 1 to 4 and Comparative Examples 1 to 5 was applied onto a silicon wafer using a spin coater so that the resultant film had a thickness of about 170 nm, and baked on a hotplate at 200° C. for 90 seconds. The resultant applied film was subjected to dry etching by $CF_4$ gas using a dry etching machine (product name: RIE-10NR, manufactured by Samco Inc.) to measure the ratio of dry etching rate of the resist underlayer film (selective ratio of dry etching rate). The results of the measurement of etching selective ratio are shown in Table 2. The larger the etching selective ratio, the faster the dry etching rate.

TABLE 2

| Example | Etching selective ratio (expressed by taking the etching selective ratio in Comparative Example 1 as 1) |
|---|---|
| Example 1 | 1.25 |
| Example 2 | 1.24 |
| Example 3 | 1.20 |
| Example 4 | 1.19 |
| Comparative Example 1 | 1.00 |
| Comparative Example 2 | 1.01 |
| Comparative Example 3 | 0.97 |
| Comparative Example 4 | 0.93 |
| Comparative Example 5 | 1.05 |

As apparent from the above results, the resist underlayer film compositions in Examples 1 to 4 gave a high etching selective ratio, i.e., a high dry etching rate, than did the resist underlayer film compositions in Comparative Examples 1 and 5. That is, the resist underlayer film compositions in Examples 1 to 4 can reduce their etching time for dry etching, making it possible to suppress such an unfavorable phenomenon as reduction of the thickness of resist film at the time of removing the resist underlayer film by dry etching. Moreover, reduction of the dry etching time can suppress etching damage that is unfavorable to the substrate for the resist underlayer film. Therefore, the film obtained from the resist underlayer film composition in the Examples is especially useful as a resist underlayer film.

[Test for Removal Properties for Film by a Resist Solvent]

Evaluation of the removal properties for film by a resist solvent (organic solvent) was made as follows. Each of the resist underlayer film-forming compositions prepared in Examples 1 to 4 was applied onto a copper substrate having a thickness of 100 nm, and heated at 200° C. for 90 seconds to form a resist underlayer film having a thickness of 170 nm. Then, the copper substrate having the resist underlayer film composition applied thereon was immersed in propylene glycol monomethyl ether (PGME) or propylene glycol monomethyl ether acetate (PGMEA), which are general resist solvents, at room temperature for one minute. The removal properties for the film after the immersion was visually observed. The results are shown in Table 3. In the case where the film was removed, the film was judged to have no resistance to the resist solvent (organic solvent), and, in the case where the film was not removed, the film was judged to have a resistance to the resist solvent.

TABLE 3

| | Removal properties for film by resist solvent | |
|---|---|---|
| Example | PGME | PGMEA |
| Example 1 | No peeling | No peeling |
| Example 2 | No peeling | No peeling |
| Example 3 | No peeling | No peeling |
| Example 4 | No peeling | No peeling |

As apparent from the above results, the film on the copper substrate given by each of the resist underlayer film compositions in Examples 1 to 4 was not removed (peeled) by PGME and PGMEA, and hence had a high chemical liquid resistance to these organic solvents (resist solvents). That is, the film obtained from each of the resist underlayer film compositions in Examples 1 to 4 can suppress an unfavorable peel phenomenon caused by a resist solvent, and therefore is useful as a resist underlayer film.

[Test for Removal Properties for Film by a Resist Developer]

Evaluation of the removal properties for film by a resist developer (aqueous alkali solution) was made as follows. Each of the resist underlayer film-forming compositions prepared in Examples 1 to 6 was applied onto a copper substrate having a thickness of 100 nm, and heated at 200° C. for 90 seconds to form a resist underlayer film having a thickness of 170 nm. Then, the copper substrate having the resist underlayer film composition applied thereon was immersed in a 2.38% by weight aqueous solution of tetramethylammonium hydroxide (TMAH) (product name: NMD-3, manufactured by Tokyo Ohka Kogyo Co., Ltd.), which is an aqueous alkali solution, at room temperature for one minute. The removal properties for the film after the immersion was visually observed. The results are shown in Table 4. In the case where the film was removed, the film was judged to have no resistance to the resist developer (aqueous alkali solution), and, in the case where the film was not removed, the film was judged to have a resistance to the resist developer.

TABLE 4

| Example | Removal properties for film by resist developer (2.38% by weight Aqueous TMAH solution) |
| --- | --- |
| Example 1 | No peeling |
| Example 2 | No peeling |
| Example 3 | No peeling |
| Example 4 | No peeling |

As apparent from the above results, the film given by each of the resist underlayer film compositions in Examples 1 to 4 on the copper substrate was not removed (peeled) by the aqueous TMAH solution, and hence had a desirable chemical liquid resistance to the resist developer (aqueous alkali solution). That is, the film obtained from each of the resist underlayer film compositions in Examples 1 to 6 is free from an unfavorable peel phenomenon by a resist developer, and therefore is useful as a resist underlayer film, which requires the development step using an aqueous alkali solution.

[Test for Removability of Film by a Wet Etching Chemical Liquid]

Evaluation of the removability of film by a wet etching chemical liquid (basic organic solvent) was made as follows. Each of the resist underlayer film-forming compositions prepared in Examples 1 to 4 and Comparative Examples 1, 3, and 5 was applied onto a copper substrate having a thickness of 100 nm, and heated at 200° C. for 90 seconds to form a resist underlayer film having a thickness of 170 nm. Then, the copper substrate having the resist underlayer film composition applied thereon was immersed in a 0.5% by weight dimethyl sulfoxide solution of tetramethylammonium hydroxide (TMAH), which is a basic organic solvent, at 50° C. for 5 minutes. The removability of the film after the immersion was visually observed. The results are shown in Table 5. In the case where the film was removed, the film was judged to have a desirable removability (releasability) by the basic organic solvent, and, in the case where the film was not removed, the film was judged to have an unsatisfactory removability (releasability) by the basic organic solvent.

TABLE 5

| Example | Removability of film by wet etching chemical liquid (0.5% by weight Dimethyl sulfoxide solution of TMAH) |
| --- | --- |
| Example 1 | Fully released |
| Example 2 | Fully released |
| Example 3 | Fully released |
| Example 4 | Fully released |
| Comparative Example 1 | No release |
| Comparative Example 3 | Partially released |
| Comparative Example 5 | Partially released |

As apparent from the above results, the resist underlayer film compositions in Examples 1 to 4 gave a film on the copper substrate with a more satisfactory removability by the wet etching chemical liquid (basic organic solvent) than did the resist underlayer film compositions in Comparative Examples 1, 3, and 5. That is, the film obtained from each of the resist underlayer film compositions in Examples 1 to 4 can exhibit a desirable removability (releasability) by the wet etching chemical liquid, and therefore is useful in the semiconductor production process, in which the resist underlayer film is removed using a wet etching chemical liquid.

[Test for Solubility of Film in a Wet Etching Chemical Liquid]

Evaluation of the solubility of film in a wet etching chemical liquid (basic organic solvent) was made as follows. Each of the resist underlayer film-forming compositions prepared in Examples 1 to 4 and Comparative Examples 1 to 5 was applied onto a silicon wafer substrate, and heated at 200° C. for 90 seconds to form a resist underlayer film having a thickness of 170 nm. Then, the formed resist underlayer film was peeled off from the substrate, and the obtained film was immersed in a 0.5% by weight dimethyl sulfoxide solution of tetramethylammonium hydroxide (TMAH), which is a basic organic solvent, at 50° C. for 5 minutes. The solubility of the film after the immersion was visually observed. The results are shown in Table 6. In the case where the film was dissolved, the film was judged to have a desirable solubility in the wet etching chemical liquid, and, in the case where the film was not dissolved (or was insoluble), the film was judged to have an unsatisfactory solubility in the wet etching chemical liquid.

TABLE 6

| Example | Solubility of film in wet etching chemical liquid (0.5% by weight Dimethyl sulfoxide solution of TMAH) |
| --- | --- |
| Example 1 | Soluble |
| Example 2 | Soluble |
| Example 3 | Soluble |
| Example 4 | Soluble |
| Comparative Example 1 | Insoluble |
| Comparative Example 2 | Insoluble |
| Comparative Example 3 | Insoluble |

TABLE 6-continued

| Example | Solubility of film in wet etching chemical liquid (0.5% by weight Dimethyl sulfoxide solution of TMAH) |
|---|---|
| Comparative Example 4 | Insoluble |
| Comparative Example 5 | Insoluble |

As apparent from the above results, the resist underlayer film compositions in Examples 1 to 4 gave a film with a more satisfactory solubility in the wet etching chemical liquid (basic organic solvent) than did the resist underlayer film compositions in Comparative Examples 1 to 5. That is, the film obtained from each of the resist underlayer film compositions in Examples 1 to 4 exhibits a desirable solubility in the wet etching chemical liquid, and therefore is useful in the semiconductor production process, in which the resist underlayer film is removed using a wet etching chemical liquid. Particularly, the film obtained from each of the resist underlayer film compositions in Examples 1 to 4 can be removed by the wet etching chemical liquid, as well as it exhibits a satisfactory solubility in the wet etching chemical liquid, and thus can prevent unfavorable contamination of the chemical liquid, which is caused by ununiform dispersion in the chemical liquid of removed film (peeled film) as foreign matter (defect). Therefore the film obtained from the resist underlayer film composition in the Examples is more useful as a resist underlayer film.

INDUSTRIAL APPLICABILITY

In the present invention, there can be provided a resist underlayer film, which has a high resistance to a resist solvent, mostly an organic solvent, and to a resist developer, an aqueous alkali solution, whereas the film further exhibits removability solely by a wet etching chemical liquid, preferably solubility solely in a wet etching chemical liquid.

The invention claimed is:

1. A resist underlayer film-forming composition comprising a solvent and a heterocyclic compound having a dicyanostyryl group, wherein the heterocyclic compound having a dicyanostyryl group is a cyclic compound containing an amide group.

2. The resist underlayer film-forming composition according to claim 1, wherein the heterocyclic compound having a dicyanostyryl group is a reaction product of an active proton compound and a heterocyclic compound precursor having an epoxy group.

3. The resist underlayer film-forming composition according to claim 1, wherein the dicyanostyryl group is represented by the following formula (1):

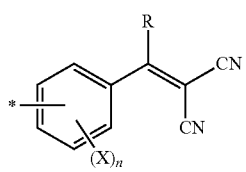

Formula (1)

wherein X represents an alkyl group, a hydroxy group, an alkoxy group, an alkoxycarbonyl group, a halogen atom, a cyano group, or a nitro group; R represents a hydrogen atom, an alkyl group, or an arylene group; n represents an integer of 0 to 4; and * indicates a bonding site to the heterocyclic compound.

4. The resist underlayer film-forming composition according to claim 1, wherein the heterocyclic compound having a dicyanostyryl group is represented by the following formula (2):

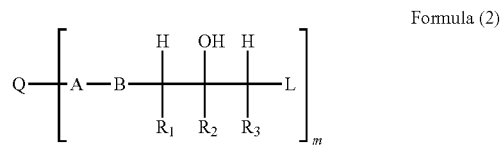

Formula (2)

wherein Q is a group resulting from eliminating m quantity of terminal atom or atoms from the heterocyclic compound, m is an integer of 1 to 4, each of m quantity of A is independently a direct bond, or an optionally branched and/or substituted alkylene group having 1 to 10 carbon atoms optionally interrupted with an ether linkage, a thioether linkage or an ester linkage, each of m quantity of B independently represents a direct bond, an ether linkage, a thioether linkage, or an ester linkage, each of m quantity of $R_1$, $R_2$ and $R_3$ independently represents a hydrogen atom, a methyl group, or an ethyl group, and each of m quantity of L is independently represented by the following formula (3):

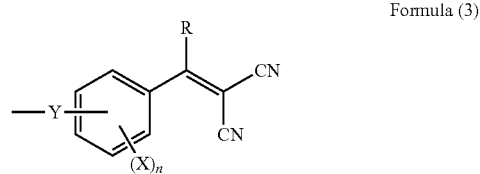

Formula (3)

wherein Y represents an ether linkage, a thioether linkage, or an ester linkage, R represents a hydrogen atom, an alkyl group, or an arylene group, n represents an integer of 0 to 4, and each of n quantity of X independently represents an alkyl group, a hydroxy group, an alkoxy group, an alkoxycarbonyl group, a halogen atom, a cyano group, or a nitro group.

5. The resist underlayer film-forming composition according to claim 1, wherein the heterocycle is triazinetrione.

6. The resist underlayer film-forming composition according to claim 4, wherein the Q in formula (2) is triazinetrione.

7. The resist underlayer film-forming composition according to claim 3, wherein the R in formula (1) is a hydrogen atom.

8. The resist underlayer film-forming composition according to claim 4, wherein the Y in formula (3) represents an ether linkage or an ester linkage.

9. The resist underlayer film-forming composition according to claim 4, wherein the A in formula (2) represents a direct bond.

10. The resist underlayer film-forming composition according to claim 1, further comprising a crosslinking agent and/or a crosslinking catalyst.

11. The resist underlayer film-forming composition according to claim 1, for use on a substrate having copper on the surface.

12. A resist underlayer film provided by removing a solvent from an applied film comprising the resist underlayer film-forming composition according to claim 1.

13. The resist underlayer film according to claim 12 formed on a substrate having copper on the surface.

14. A method for producing a patterned substrate, comprising the steps of:
applying the resist underlayer film-forming composition according to claim 1 onto a substrate having copper on the surface and baking the applied composition to form a resist underlayer film;
applying a resist onto the resist underlayer film and baking the applied resist to form a resist film;
subjecting the semiconductor substrate covered with the resist underlayer film and the resist to exposure; and
subjecting the resist film obtained after exposure to development and patterning.

15. A method for producing a semiconductor device, comprising the steps of:
forming a resist underlayer film comprising the resist underlayer film-forming composition according to claim 1 on a substrate having copper on the surface;
forming a resist film on the resist underlayer film;
irradiating the resist film with a light or an electron beam and subjecting the resultant resist film to development to form a resist pattern;
then removing the resist underlayer film exposed between the resist pattern;
performing copper plating in the formed resist pattern; and
removing the resist pattern and the resist underlayer film present under the resist pattern.

16. The method according to claim 15, wherein at least one of the steps of removing the resist underlayer film is conducted by a wet treatment.

* * * * *